(12) United States Patent
Quintanilha et al.

(10) Patent No.: US 10,101,671 B2
(45) Date of Patent: Oct. 16, 2018

(54) METROLOGY METHODS, METROLOGY APPARATUS AND DEVICE MANUFACTURING METHOD

(71) Applicant: ASML Netherlands B.V., Veldhoven (NL)

(72) Inventors: Richard Quintanilha, Eindhoven (NL); Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/388,601

(22) Filed: Dec. 22, 2016

(65) Prior Publication Data

US 2017/0184981 A1    Jun. 29, 2017

(30) Foreign Application Priority Data

Dec. 23, 2015 (EP) ..................... 15202273

(51) Int. Cl.
*G03F 7/20* (2006.01)
*H05G 2/00* (2006.01)
(Continued)

(52) U.S. Cl.
CPC ..... *G03F 7/70633* (2013.01); *G01N 21/8806* (2013.01); *G01N 21/956* (2013.01);
(Continued)

(58) Field of Classification Search
CPC ............ G03F 7/70625; G03F 7/70491; G03F 7/70616; G03F 7/70633; G03F 7/70683;
(Continued)

(56) References Cited

U.S. PATENT DOCUMENTS 7,403,293 B2    7/2008  Pellemans et al.
9,494,535 B2    11/2016 Sezginer et al.
(Continued)

FOREIGN PATENT DOCUMENTS

CN    105549341 A    5/2016
JP    2000-241113 A   9/2000
(Continued)

OTHER PUBLICATIONS

International Search Report and Written Opinion of the International Searching Authority directed to related International Patent Application No. PCT/EP2016/080058, dated Apr. 19, 2017; 15 pages.
(Continued)

*Primary Examiner* — Michelle M Iacoletti
(74) *Attorney, Agent, or Firm* — Sterne, Kessler, Goldstein & Fox P.L.L.C.

(57) ABSTRACT

Hybrid metrology apparatus (1000, 1100, 1200, 1300, 1400) measures a structure (T) manufactured by lithography. An EUV metrology apparatus (244, IL1/DET1) irradiates the structure with EUV radiation and detects a first spectrum from the structure. Another metrology apparatus (240, IL2/DET2) irradiates the structure with second radiation comprising EUV radiation or longer-wavelength radiation and detects a second spectrum. Using the detected first spectrum and the detected second spectrum together, a processor (MPU) determines a property (CD/OV) of the structure. The spectra can be combined in various ways. For example, the first detected spectrum can be used to control one or more parameters of illumination and/or detection used to capture the second spectrum, or vice versa. The first spectrum can be used to distinguish properties of different layers (T1, T2) in the structure. First and second radiation sources (SRC1, SRC2) may share a common drive laser (LAS).

20 Claims, 10 Drawing Sheets

(51) Int. Cl.
*G01N 21/956* (2006.01)
*G01N 21/88* (2006.01)

(52) U.S. Cl.
CPC ........ *G03F 7/7065* (2013.01); *G03F 7/70625* (2013.01); *H05G 2/008* (2013.01); *G01N 2021/95676* (2013.01)

(58) Field of Classification Search
CPC ............. G03F 7/70516; G03F 7/70591; G03F 7/70566; G03F 7/7085; G03F 7/2004; G03F 7/705; G03F 7/70558; H01L 22/12; G01N 21/9501; G01N 21/956; G01N 21/4788; G01N 21/93; G01N 2021/95676; G01N 21/47; G01N 21/8806; G01N 23/2251; G01N 21/4738; G01N 21/65; G01N 2223/611; G01N 2223/6116
See application file for complete search history.

(56) References Cited

U.S. PATENT DOCUMENTS

| | | |
|---|---|---|
| 2003/0010912 A1 | 1/2003 | Archie |
| 2004/0137651 A1 | 7/2004 | Smedt et al. |
| 2004/0257572 A1 | 12/2004 | Stacker |
| 2005/0195398 A1 | 9/2005 | Adel et al. |
| 2006/0066855 A1 | 3/2006 | Boef et al. |
| 2007/0224518 A1 | 9/2007 | Yokhin et al. |
| 2008/0246951 A1 | 10/2008 | Walsh et al. |
| 2008/0273662 A1 | 11/2008 | Yun et al. |
| 2009/0279090 A1 | 11/2009 | Wolf et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | De Kerkhof et al. |
| 2012/0044470 A1 | 2/2012 | Smilde et al. |
| 2012/0123581 A1 | 5/2012 | Smilde et al. |
| 2013/0215404 A1 | 8/2013 | Den Boef |
| 2013/0242303 A1 | 9/2013 | Liu |
| 2013/0245806 A1 | 9/2013 | Vaid et al. |
| 2013/0258310 A1 | 10/2013 | Smilde et al. |
| 2013/0271740 A1 | 10/2013 | Quintanilha |
| 2013/0304424 A1 | 11/2013 | Bakeman et al. |
| 2014/0019097 A1 | 1/2014 | Bakeman et al. |
| 2014/0060148 A1 | 3/2014 | Amit et al. |
| 2014/0241610 A1 | 8/2014 | Duffy et al. |
| 2014/0273299 A1 | 9/2014 | Vaicl et al. |
| 2014/0297211 A1 | 10/2014 | Pandev et al. |
| 2015/0032398 A1 | 1/2015 | Peterlinz et al. |
| 2015/0051877 A1 | 2/2015 | Bakeman et al. |
| 2015/0138523 A1 | 5/2015 | Jak et al. |
| 2015/0176985 A1 | 6/2015 | Shchegrov et al. |
| 2015/0177135 A1 | 6/2015 | Amit et al. |
| 2015/0235108 A1 | 8/2015 | Pandev |
| 2015/0323316 A1 | 11/2015 | Shchegrov et al. |
| 2015/0323471 A1 | 11/2015 | Sapiens et al. |
| 2016/0003609 A1 | 1/2016 | Shchegrov et al. |
| 2016/0109230 A1 | 4/2016 | Pandev et al. |
| 2016/0117812 A1 | 4/2016 | Pandev et al. |
| 2016/0117847 A1 | 4/2016 | Pandev et al. |
| 2016/0139065 A1 | 5/2016 | Barak et al. |
| 2016/0141193 A1 | 5/2016 | Pandev et al. |
| 2016/0202193 A1 | 7/2016 | Hench et al. |
| 2016/0282282 A1 | 9/2016 | Quintanilha et al. |

FOREIGN PATENT DOCUMENTS

| | | |
|---|---|---|
| TW | 201543003 A | 11/2015 |
| WO | WO 2014/194095 A1 | 12/2014 |
| WO | WO 2015/125127 A1 | 8/2015 |
| WO | WO 2016/150957 A1 | 9/2016 |

OTHER PUBLICATIONS

Nakasuji, et al., "Development of Coherent Extreme-Ultraviolet Scatterometry Microscope with High-Order Harmonic Generation Source for Extreme-Ultraviolet Mask Inspection and Metrology," Japanese Journal of Applied Physics, vol. 51, Jun. 20, 2012; 6 pages.
Constantoudis et al., "Model-aided hybrid metrology for surface roughness measurement fusing AFM and SEM data", EDP Sciences, 17th International Congress of Metrology, 14005 (2015); 8 pages.
Danylyuk et al., "Multi-angle spectroscopic EUV reflectometry for analysis of thin films and interfaces", Wiley-VCH, Physica Status Solidi (2015); 6 pages.
Hossain et al., "XPS-XRF Hybrid Metrology enabling FDSOI Process", Proc. of SPIE, vol. 9778 (2016); 8 pages.
Lemaillet et al., "Intercomparison between optical and x-ray scatterometry measurements of FinFET structures", Proc. of SPIE, vol. 8681 (2013); 8 pages.
Leray et al., "Hybrid Overlay Metrology for High order correction by using CDSEM", Proc. of SPIE, vol. 9778 (2016); 8 pages.
Leray et al., "Hybrid Overlay metrology with CDSEM in a BEOL patterning scheme", Proc. of SPIE, vol. 9424 (2015); 8 pages.
Osorio et al., "Hybrid metrology implementation: server approach", Proc. of SPIE, vol. 9424 (2015); 13 pages.
Silver et al., "Optimizing Hybrid Metrology through a Consistent Multi-Tool Parameter Set and Uncertainty Model", Proc. of SPIE, vol. 9050 (2014); 8 pages.
Vaid et al., "Hybrid metrology co-optimization of critical dimension scanning electron microscope and optical critical dimension", Journal of Micro/Nanolithography, MEMS, and MOEMS, vol. 13(4) (2014); 9 pages.

METROLOGY METHODS, METROLOGY APPARATUS AND DEVICE MANUFACTURING METHOD

BACKGROUND

Field of the Invention

The present invention relates to methods and apparatus for metrology usable, for example, in the manufacture of devices by lithographic techniques and to methods of manufacturing devices using lithographic techniques. Methods of measuring critical dimension (line width) are described, as a particular application of such metrology. Methods of measuring asymmetry-related parameters such as overlay are also described.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer).

In lithographic processes, it is desirable frequently to make measurements of the structures created, e.g., for process control and verification. Various tools for making such measurements are known, including scanning electron microscopes (SEM), which are often used to measure critical dimension (CD). Other specialized tools are used to measure parameters related to asymmetry. One of these parameters is overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis. Compared with SEM techniques, optical scatterometers can be used with much higher throughput, on a large proportion or even all of the product units.

The targets used by conventional scatterometers are relatively large, e.g., 40 µm by 40 µm, gratings and the measurement beam generates a spot that is smaller than the grating (i.e., the grating is underfilled). In order to reduce the size of the targets, e.g., to 10 µm by 10 µm or less, e.g., so they can be positioned in amongst product features, rather than in the scribe lane, so-called "small target" metrology has been proposed, in which the grating is made smaller than the measurement spot (i.e., the grating is overfilled). These targets can be smaller than the illumination spot and may be surrounded by product structures on a wafer. Typically small targets are used for measurement of overlay and other performance parameters that can be derived from measurements of asymmetry in the grating structure. By placing the target in among the product features ("in-die target"), it is hoped to increase accuracy of measurement. The improved accuracy is expected for example because the in-die target is affected by process variations in a more similar way to the product features, and less interpolation may be needed to determine the effect of a process variation at the actual feature site. These optical measurements of overlay targets have been very successful in improving overlay performance in mass production. So-called dark-field imaging has been used for this purpose. Examples of dark field imaging metrology can be found in international patent applications US20100328655A1 and US2011069292A1 which documents are hereby incorporated by reference in their entirety. Further 10 developments of the technique have been described in published patent publications US20110027704A, US20110043791A, US2011102753A1, US20120044470A, US20120123581A, US20130258310A, US20130271740A and US2015138523. Similar small target techniques for focus performance and dose performance have been implemented also. The content of all these prior application is incorporated herein by reference.

As technology develops, however, performance specifications become ever tighter. Moreover, small target techniques have not been developed for measurement of other parameters such as line width or critical dimension (CD). A further limitation of current methods is that they are made with optical wavelengths, much greater than the typical dimensions of real product features. A particular parameter of interest is linewidth (CD). CD metrology suffers from low accuracy, cross-talk between parameters of interest and also between parameters of interest and other hidden parameters (process robustness). As the microscopic structures shrink and become more and more complex in geometry (going to 3-D structures, for example), known techniques of CD metrology struggle to provide accuracy, precision, and speed. Another parameter of interest is overlay.

As an alternative to optical metrology methods, it has also been considered to use X-rays to measure overlay in a semiconductor device. One technique is known as transmissive small angle X-ray scattering or T-SAXS. A T-SAXS apparatus applied to measurement of overlay is disclosed in US 2007224518A (Yokhin et al, Jordan Valley), and the contents of that application are incorporated herein by reference. Profile (CD) measurements using T-SAXS are discussed by Lemaillet et al in "Intercomparison between optical and X-ray scatterometry measurements of FinFET structures", Proc. of SPIE, 2013, 8681. T-SAXS uses X-rays of wavelength less than 1 nm, for example in the range 0.01 m to 1 nm, and so targets for T-SAXS can be made of product-like features. T-SAXS signals tend to be very weak, especially when the target size is small. Therefore the measurements tend to be too time-consuming for use in high-volume manufacturing. T-SAXS apparatus can be used to measure targets small enough to be considered for placement among the product features. Unfortunately, the small target size requires a small spot size and consequently even longer measurement times.

Published patent applications US 20130304424A1 and US2014019097A1 (Bakeman et al/KLA) describe hybrid metrology techniques in which measurements made using x-rays and "optical" measurements with wavelengths in the range 120 nm and 2000 nm are combined together to obtain a measurement of a parameter such as CD. A CD measurement is obtained by coupling and x-ray mathematical model and an optical mathematical model through one or more common.

Reflectometry techniques using X-rays (GI-XRS) and extreme ultraviolet (EUV) radiation at grazing incidence are known for measuring properties of films and stacks of layers on a substrate. Within the general field of reflectometry, goniometric and/or spectroscopic techniques can be applied. In goniometry, the variation of a reflected beam with different incidence angles is measured. Spectroscopic reflectometry, on the other hand, measures the spectrum of wavelengths reflected at a given angle (using broadband radiation). For example, EUV reflectometry has been used for inspection of mask blanks, prior to manufacture of reticles (patterning devices) for use in EUV lithography. Work on these techniques has been described for example by S Danylyuk et al in "Multi-angle spectroscopic EUV reflectometry for analysis of thin films and interfaces", Phys. Status Solidi C 12, 3, pp. 318-322 (2015). However, such measurements are different from the measurement of CD in a periodic structure. Moreover, particularly in view of the very shallow grazing incidence angles involved, none of these known techniques is suitable for metrology on small targets such as an in-die grating.

In a European patent application 15160786, not published at the present priority date, it is proposed to measure properties such as CD and overlay of target structures using EUV radiation, that is radiation in the wavelength range from about 1 nm to about 100 nm. Spectroscopic reflectometry is performed using radiation scattered at zero and/or higher diffraction orders. A smaller spot size is achieved than in T-SAXS or GI-SAXS methods, using a higher grazing angle of incidence than can be used at x-ray wavelengths. Diffraction signals are further strengthened by the use of a conical mount between an EUV optical system and the substrate. This allows a non-zero azimuthal angle of incidence relative to a direction of periodicity of the target structure. The contents of the prior application are hereby incorporated by reference in the present disclosure.

In the mentioned patent application, a form of hybrid metrology is proposed in which larger targets with product-like structures are measured using the EUV radiation, while smaller in-die targets are measured using an angle-resolved scatterometer working in a more conventional optical waveband. The results of the EUV measurements on a few substrates are used to calibrate the optical measurements in high-volume manufacture.

SUMMARY OF THE INVENTION

The invention aims to provide alternative methods and apparatus for metrology for determining properties of microscopic structures of the type found in semiconductor manufacturing.

The invention in a first aspect provides a hybrid metrology apparatus for measuring a property of a structure manufactured by a lithographic process, the hybrid metrology apparatus comprising:

(a) a first illumination system for irradiating the structure with first radiation, the first radiation comprising one or more wavelengths in the range 1 nm to 100 nm;

(b) a first detection system for detecting a first spectrum comprising at least part of the first radiation reflected by the periodic structure;

(c) a second illumination system for irradiating the structure with second radiation, the second radiation comprising one or more wavelengths in the range 1 nm to 100 nm or in the range 100 nm to 1000 nm;

(d) a second detection system for detecting a second spectrum comprising at least part of the second radiation reflected by the periodic structure;

(e) a processing system for using the detected first spectrum and the detected second spectrum to determine a property of the structure.

The inventors have recognized that radiation in the extreme ultraviolet (EUV) waveband offers particular advantages for metrology of CD, overlay and other properties of small metrology targets. Conveniently these small metrology targets may again have the form of periodic structures. Compared with the optical scatterometry commonly practiced, EUV rays will not be strongly influenced by underlying features, and modeling of the periodic structure itself can be more accurate as a result. Compared with X-rays, there is potential to focus the EUV radiation to a finer spot without undue loss of power. Compared with X-rays, there is potential to use a much higher angle of incidence. By providing in addition a suitable EUV optical system for illumination and detection of the target, EUV radiation can be formed into a small enough spot for in-die metrology, even when the spot is elongated by the grazing incidence. In order to obtain sufficient information for CD metrology, spectral properties across a range of EUV wavelengths can be measured.

Reference to a range of wavelengths from 1 nm to 100 nm is not intended to mean that the apparatus or method should use wavelengths across that entire wave range, or even be capable of doing so. An individual implementation may choose to work with wavelengths over only a subset of the range. The appropriate range will depend on the availability of suitable sources, and the dimension of structures to be measured.

In accordance with the first aspect of the invention as set forth above, the EUV metrology apparatus may be used to supplement a second metrology apparatus, which may operate in a different manner within the same waveband, or may operate in a different waveband. Different modes of combining the detected spectra can be envisaged, some of which will be explained and illustrated in the embodiments below.

In a particular implementation, the metrology system includes a substrate support adapted to receive semiconductor wafers (for example 300 mm wafers) from an automated wafer handler.

In a second aspect of the invention, there is provided a method of measuring a property of a structure manufactured by a lithographic process, the method comprising:

(a) irradiating the structure with first radiation, the first radiation comprising one or more wavelengths in the range 1 nm to 100 nm;

(b) detecting a first spectrum comprising at least part of the first radiation reflected by the periodic structure;

(c) irradiating the structure with second radiation, the second radiation comprising one or more wavelengths in the range 1 nm to 100 nm or in the range 100 nm to 1000 nm;

(d) detecting a second spectrum comprising at least part of the second radiation reflected by the periodic structure;

(e) using the detected first spectrum and the detected second spectrum to determine a property of the structure.

The invention further provides a device manufacturing method comprising:

transferring a pattern from a patterning device onto a substrate using a lithographic process, the pattern defining at least one periodic structure;

measuring one or more properties of the periodic structure to determine a value for one or more parameters of the lithographic process; and applying a correction in subsequent operations of the lithographic process in accordance with the measured property, wherein the step of measuring the properties of the periodic structure includes measuring a property using a hybrid metrology system or method according to the aspects of the invention set forth above.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example, with reference to the accompanying drawings in which.

DETAILED DESCRIPTION OF EXEMPLARY EMBODIMENTS

Before describing embodiments of the invention in detail, it is instructive to present an example environment in which embodiments of the present invention may be implemented.

Figure 1:
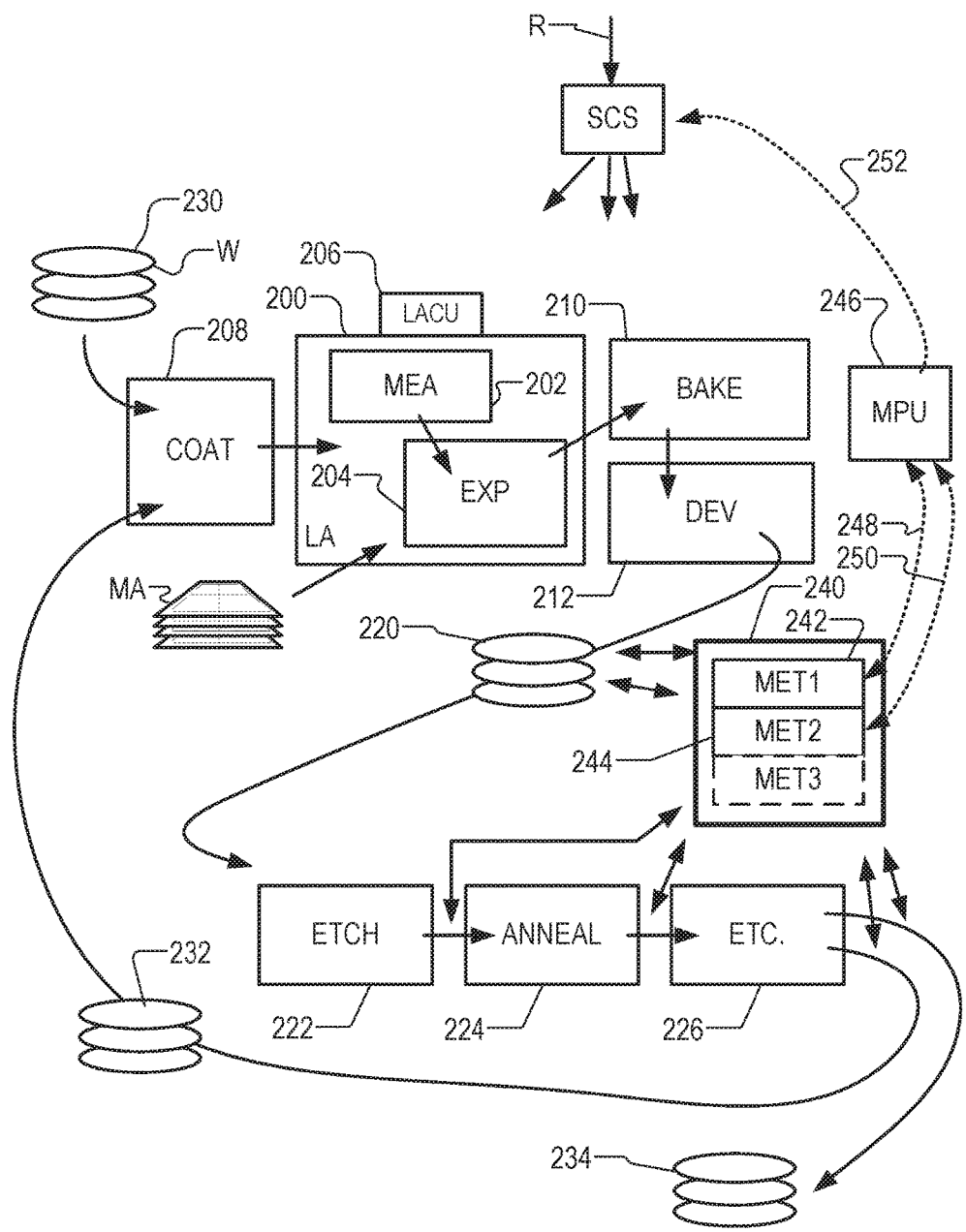
FIG. 1 depicts a lithographic apparatus together with other apparatuses forming a production facility for semiconductor devices, and including a hybrid metrology apparatus according to an embodiment of the present invention.

FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of ma4ny marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes hybrid metrology system 240 which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Using the hybrid metrology system 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, hybrid metrology system 240 and/or other metrology apparatuses (not shown) can be applied to measure properties of the processed substrates 232, 234, and incoming substrates 230.

Each generation of lithographic manufacturing technology (commonly referred to as a technology "node") has tighter specifications for performance parameters such as CD. One of the main challenges in metrology is that the metrology target size is desired to be smaller than the targets customarily used with metrology apparatus 240. For example, a present goal is to use targets with a size of 5 µm×5 µm or smaller. These small sizes would permit wider use of so-called "in-die" or "on product" metrology, where targets are located among the product features (instead of being confined in scribe lane areas between product areas). The only metrology technique currently used for in-die CD metrology is electron microscopy (CD-SEM). This known technique shows limitations for future nodes, and only provides very limited geometrical information of the structure.

Within hybrid metrology system 240, a first metrology apparatus 242 (MET1) and second metrology apparatus 244 (MET2) and optionally further apparatuses (MET3 etc.) are provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Hybrid metrology system 240 differs from the known example in that multiple types of measurement can be performed within the hybrid metrology system to obtain a better overall measurement of a parameter or parameters of interest on a given target structure.

Each of the metrology apparatuses 242, 244 can have a particular illumination system for radiation of a particular characteristic. More detailed examples of the types of apparatuses that can be combined will be given below. In each case, metrology processing system 246 receives first spectrum data 248 from a first detection system within the first metrology apparatus 242 and receives second spectrum data 250 from a second detection system within the second metrology apparatus 244. Metrology processing system 246 combines these spectra in a hybrid calculation obtain the measurements 252 of CD or other parameters that are reported to the supervisory control system SCS. In some embodiments, metrology processing system 246 also controls operation of one or more of the metrology apparatuses 242, 244 to vary parameters of its operation, based on to spectrum data received from the other one of the metrology apparatuses.

One of the apparatuses within the hybrid metrology system, for example the second metrology apparatus 244, may be designed to operate with radiation at visible or UV wavelengths, while another of the apparatuses, for example the first metrology apparatus 242 may be designed to operate with EUV radiation. In other embodiments, both the first and second metrology apparatuses may be designed to operate with EUV radiation, of the same or different wavelengths. One of the apparatuses may be designed to operate with grazing incidence while another is designed to operate with normal or near-normal incidence. One of the apparatuses may be designed to obtain a frequency-resolved spectrum of radiation scattered by the target structure, while another of the apparatuses is designed to obtain an angle-resolved spectrum. One of the metrology apparatuses, for example the second metrology apparatus 244 may be an angle-resolved scatterometer, a spectroscopic scatterometer, a spectroscopic ellipsometer, and/or a spectroscopic Mueller ellipsometer. Common hardware can be used to implement more than one of these types of metrology apparatus. These and other variants can be used in the hybrid metrology system to obtain more information about a structure, and so give more accurate measurements of a parameter of interest. Three or more metrology apparatuses can be provided within hybrid metrology system, and the first and second metrology apparatuses are labeled here only for convenience. These additional metrology apparatuses can be used all together in making one measurement, or they may be used in different sub-combinations.

In embodiments of the hybrid metrology system 240 according to the present disclosure, it is proposed to use EUV wavelengths for metrology in at least one of the metrology apparatuses. In some embodiments, EUV reflectometry, in particular spectroscopic EUV reflectometry, is employed as part of the CD-metrology solution for future technological nodes. In the pending European patent application number 15160786, mentioned above, it is demonstrated that EUV reflectometry offers benefits of high sensitivity, being robust against process variations and being selective for a parameter of interest.

Like the optical scatterometer used in today's production facilities, EUV metrology apparatus can be used to measure structures within the resist material treated within the litho cell (After Develop Inspection or ADI), and/or to measure structures after they have been formed in harder material (After Etch Inspection or AEI). For example, substrates may be inspected using EUV metrology apparatus 242 after they have been processed by the developing apparatus 212, etching apparatus 222, annealing apparatus 224 and/or other apparatus 226. By contrast, X-ray techniques will generally be limited to AEI and cannot be used to measure structures formed only in the resist. This restricts the possibility to re-work substrates if they fail an inspection.

EUV Spectroscopic Reflectometry

Figure 2:
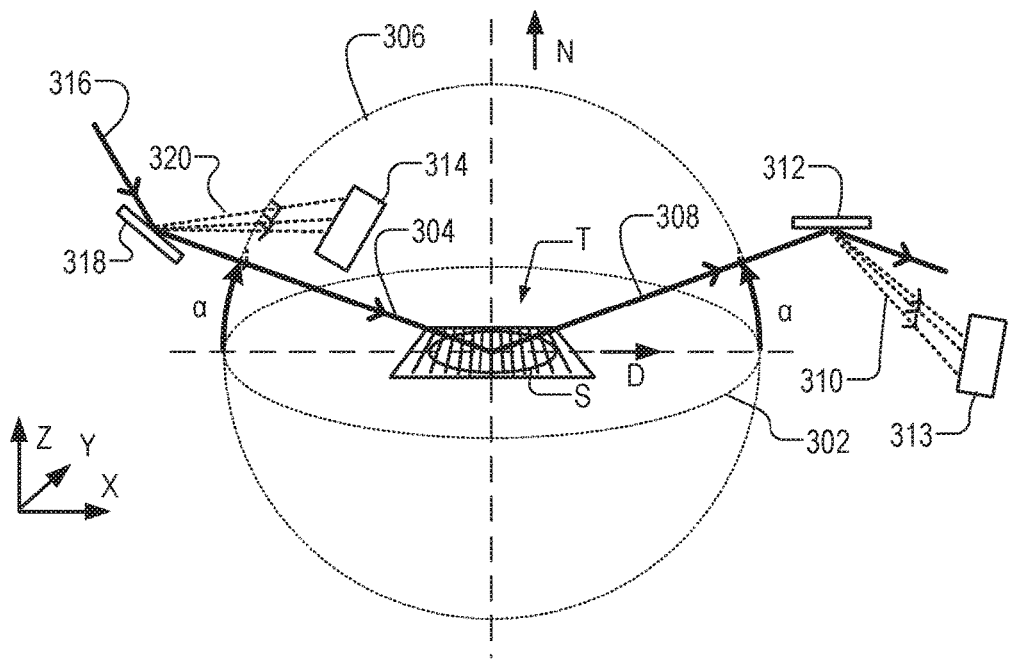
FIG. 2 illustrates the geometry of incident and reflected rays in relation to a grating target in an EUV metrology section in one embodiment of the hybrid metrology apparatus of FIG. 1.
Figure 3:
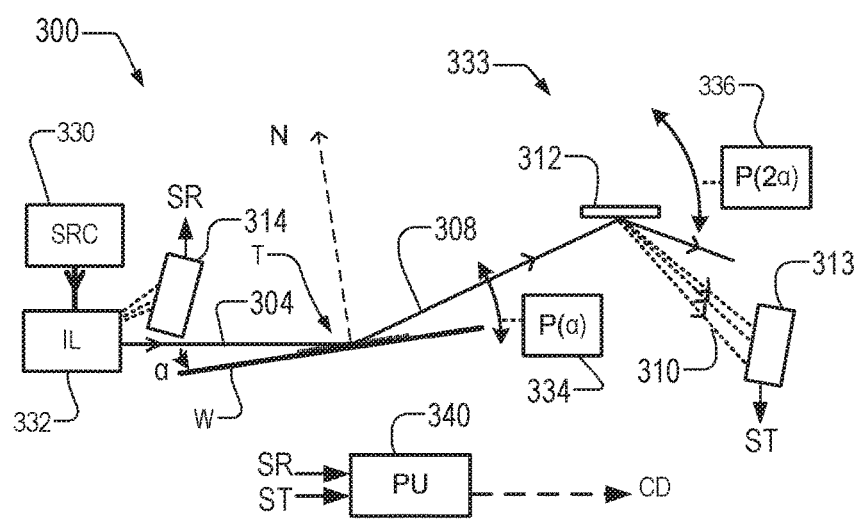
FIG. 3 illustrates schematically the components of an EUV metrology apparatus, performing the EUV metrology method of FIG. 2.

FIG. 2 illustrates an EUV metrology method while FIG. 3 illustrates an EUV metrology apparatus 300. The apparatus can be used as an example of the first metrology apparatus 242 or second metrology apparatus 244 for measuring parameters of substrates W processed in the production facility of FIG. 1.

In FIG. 2, the target T is represented schematically as comprising a one-dimensional grating structure at the origin of a spherical reference frame. Axes X, Y and Z are defined relative to the target. (Of course any arbitrary coordinate system can be defined in principle, and each component may have its own local reference frame, that can be defined relative to the one shown.) The direction of periodicity D of the target structure is aligned with the X axis. The drawing is not a true perspective drawing, but a schematic illustration only. The X-Y plane is the plane of the target and substrate, and for clarity is shown tilted toward the viewer, represented by an oblique view of circle 302. The Z direction defines the direction N normal to the substrate. In FIG. 2, one of the incident rays is labeled 304 and has an angle α of grazing incidence. In this example, the incident ray 304 (and all incident rays forming the radiation spot S) lie substantially in a plane parallel to the X-Z plane, that is a plane defined by the directions D and N and represented by circle 306. A reflected ray 308 that is not scattered by the periodic structure of the target T emerges towards the right hand side of the target in the diagram, with an elevation angle α.

To perform spectroscopic reflectometry, ray 308 and other reflected rays are broken into a spectrum 310, comprising rays of different wavelengths. The spectrum may be produced for example using a grazing incidence diffraction grating 312. The spectrum is detected by a detector 313. This detector, which may for example be a CCD image detector having an array of pixels, is used to transform the spectrum into electrical signals and eventually digital data for analysis.

In a practical system, the spectrum of radiation 304 may be subject to time variations, which would disturb the analysis. In order to normalize the detected spectrum against these variations, a reference spectrum is captured by a second detector 314. To produce the reference spectrum, source radiation 316 is diffracted by another diffraction grating 318. A zero order reflected ray of grating 318 forms the incident ray 304, while the first order diffracted rays 320 of grating 318 form the reference spectrum detected by reference spectrum detector 314. Electrical signals and data representing the reference spectrum are obtained for use in the analysis.

From the measured spectrum, obtained for one or more values of incidence angle α, a measurement of a property of the target structure T can be calculated. In the hybrid metrology system 240, this measurement is obtained by using the detected spectrum in combination with one or more spectra detected by other metrology apparatuses on the same target structure. Different ways of making this combination are described further below.

Turning to FIG. 3, EUV metrology apparatus 300 is provided for measuring properties of a metrology target T formed on substrate W, by the method of FIG. 2. Various hardware components are represented schematically. The practical implementation of these components can be performed by the relevant skilled persons applying a mixture of existing components and specially-designed components, according to well-known design principles. A support (not shown in detail) is provided for holding the substrate at a desired position and orientation relative to other components to be described. A radiation source 330 provides radiation to an illumination system 332. Illumination system 332 provides a beam of EUV radiation represented by ray 304 which forms a focused irradiation spot on target T. Illumination system 332 also provides the reference spectrum 320 to detector 314. Components 312, 313 etc. may be conveniently considered as a detection system 333.

Substrate W in this example is mounted on a movable support having a positioning system 334 such that an angle of incidence α of ray 304 can be adjusted. In this example, it is chosen as a matter of convenience to tilt the substrate W to change the incidence angle, while the source 330 and illumination system 332 remain stationary. In order to catch the reflected ray 308, detection system 333 is provided with a further movable support 336, so that it moves through an angle 2α relative to the stationary illumination system, or through an angle α relative to the substrate. In the grazing incidence regime of reflectometry, it is convenient to define the incidence angle α by reference to the plane of the substrate, as shown. Of course, it could equally be defined as an angle between the direction of incidence of incident ray I and a direction N normal to the substrate.

Additional actuators, not shown, are provided for bringing each target T into a position where the focused spot S of radiation is located. (Looking at it another way, to bring the spot to the position where the target is located.) In a practical application, there may be a succession of individual targets or target locations to be measured on a single substrate, and a succession of substrates too. It is immaterial, in principle, whether the substrate and target are moved and reoriented while the illumination system and detector stay still, or whether the substrate stays still while the illumination system and detector are moved, or whether different components of the relative movement are achieved by a combination of these techniques. The present disclosure encompasses all these variants.

As already described with reference to FIG. 2, the radiation reflected by target T and substrate W is split into a spectrum 310 of rays of different wavelengths, before it impinges on detector 313. Detector 306 comprises for example a position-sensitive EUV detector, typically an array of detector elements. The array may be a linear array, but in practice a 2-dimensional array of elements (pixels) may be provided. Detector 313 may be for example a CCD (charge coupled device) image sensor.

A processor 340, which may be part of the metrology processing system 246 or a sub-system local to the metrology apparatus 300, receives signals from the detectors 313 and 314. In particular, signal ST from detector 313 represents the target spectrum and signal SR from detector 314 represents the reference spectrum. Processor 340 can subtract the reference spectrum from the target spectrum to contain a reflection spectrum of the target, normalized against variation in the source spectrum. The resulting reflection spectra for one or more angles of incidence are used in the processor 340 to calculate indirectly a measurement of property of the target, for example CD or overlay.

In practice, radiation from source 330 may be provided in a series of short pulses and signals SR and ST may be captured together for each pulse. Difference signals for each individual pulse are calculated, before being aggregated into an overall reflection spectrum for this target at this angle of incidence. In this way, instability of the source spectrum between pulses is corrected for. The pulse rate may be thousands, or even tens of thousands per second (hertz). The number of pulses aggregated to measure one reflection spectrum may be tens or hundreds, for example. Even with so many pulses, the physical measurement takes a fraction of one second.

In the application of this EUV-SR to metrology in semiconductor manufacturing, small grating targets can be used. Multiple diffraction spectra are captured using detectors 313 and 314, while setting the grazing angle of incidence α to various different values. Using the detected spectra and a mathematical model of the target structure, reconstruction calculations can be performed to arrive at measurement of CD and/or other parameters of interest. An example reconstruction method is illustrated in the pending application. In the hybrid metrology system that is the subject of the present disclosure, the reconstruction method is modified to take account of spectra detected by two or more metrology apparatuses, and not only the one illustrated in FIG. 3.

Considering briefly the target itself, dimensions of the lines and spaces will depend on the target design, but the period of the structure may be for example less than 100 nm, less than 50 nm, less than 20 nm, even less than 10 nm and down to 5 nm. The lines of the grating structure may be of the same dimension and pitch as product features in a product area of the substrate. The lines of the grating structure may in fact be the lines of a product structure, rather than a target structure formed, within a dedicated target area, solely for the purposes of metrology. Such small features may be formed for example in an EUV lithography process, by imprint lithography or by direct-write methods. Such small features may also be formed using present-day DUV lithography, by a so-called double-patterning processes (generally multiple-patterning). Techniques in this category include pitch-doubling, for example by litho-etch-litho-etch (LELE) and self-aligned dual-damascene in back end-of the line (BEOL) layers. For the purposes of explanation, it will be assumed in the following examples that CD is the parameter of interest. However, where there are two gratings formed on top of one another, another parameter of interest maybe overlay. This can be measured based on asymmetry in the EUV-SR diffraction orders, as described separately below. The incidence angle can be elevated if necessary to achieve adequate penetration to the lower structure.

In the multiple-patterning process, structures are formed in one layer of the product not in one patterning operation but in two or more patterning steps. Thus, for example, a first population of structures may be interleaved with a second population of structures, and the populations are formed in different steps, so as to achieve a higher resolution than one step alone can produce. While the placement of the populations should be identical and perfect in relation to other features on the substrate, of course every real pattern exhibits a certain positional offset. Any unintentional positional offset between the populations can be regarded as a form of overlay, and can be measured by analogous techniques to those used to measure overlay between layers. Additionally, overlay against features in an underlying or overlying layer can be different for each population when multiple populations of features are formed in a single layer, and overlay for each of these populations can be measured separately if desired.

Figure 4A:
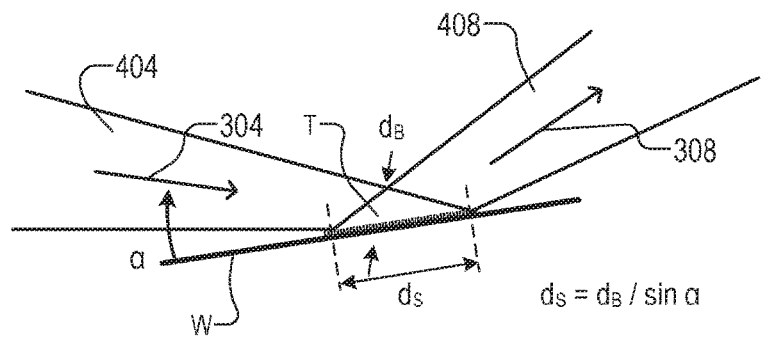
FIG. 4A illustrates by a schematic side view the elongation of a spot of radiation under grazing incidence, with schematic representations of beam cross-section B an spot S shown schematically at 4B and 4C for different angles of incidence.

FIG. 4 illustrates the problem of elongation of a radiation spot, which is challenging for implementation of in-die metrology using grazing incidence reflectometry. In FIG. 4(a), the substrate W and target T are shown in cross-section. Representative incident ray 304 and reflected ray 308 are illustrated, with incidence angle α relative to substrate W. As these are representative rays, it should be considered that the incident radiation as a whole comprises many rays, which form a beam indicated schematically at 404. Similarly, the reflected radiation comprises many rays 308 which form a beam indicated schematically at 408. In order to make use of the smallest possible target, a radiation spot is formed by focusing the rays of the beam 404, so that they converge to define a minimum beam diameter precisely where they meet the surface of substrate W. In the illustration, the incident beam 404 is convergent to a focus with a minimum diameter dB. The reflected beam 408 (ignoring scattering effects) comprises divergent rays, as shown. Because grazing incidence angle α is relatively small (in other words, nearer to zero than to 90°) the diameter dS of the radiation beam 404, as projected on to the target T, is several times greater than the beam diameter dB. The ratio between diameters dS and dB depends on the sine of angle α as shown in FIG. 4(a).

Figure 4B:
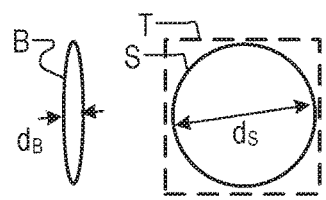
Figure 4C:
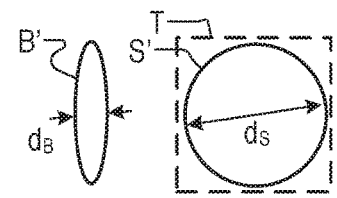

As shown in FIG. 4(b), to achieve circular spot S that fits within the area of target T, the beam 404 should have the strongly elliptical cross section shown at B. When the angle α is 5°, for example, the minimum diameter dB of the beam should be more than ten times smaller than the allowable diameter of the spot dS (sin 5°=0.087). For lower angles of incidence, the minimum diameter of the beam would have to be tens, hundreds or even thousands of times smaller. To obtain a spot that fits within a small target area such as 5 µm square would be impossible in practice. Even at α=5°, the minimum beam diameter dB should be around 436 nm to achieve a spot size under 5 µm. Conversely, as seen in FIG. 4(c), an increase in the grazing incidence angle α greatly relaxes the minimum diameter requirement of the beam 404. The ellipse B' can be much broader than the ellipse B, in order to achieve a spot S' that fits within the area of target T. For example, for α=20°, the beam diameter will be increased only by a factor of three. The minimum diameter dB can be as large as 1.7 µm without exceeding the 5 µm spot size. Compared with known techniques, particularly X-ray reflectometry (GI-XRS), the inventors have recognized that use of these higher incidence angles can bring smaller spot sizes within the capability of EUV optical design.

Figure 5:
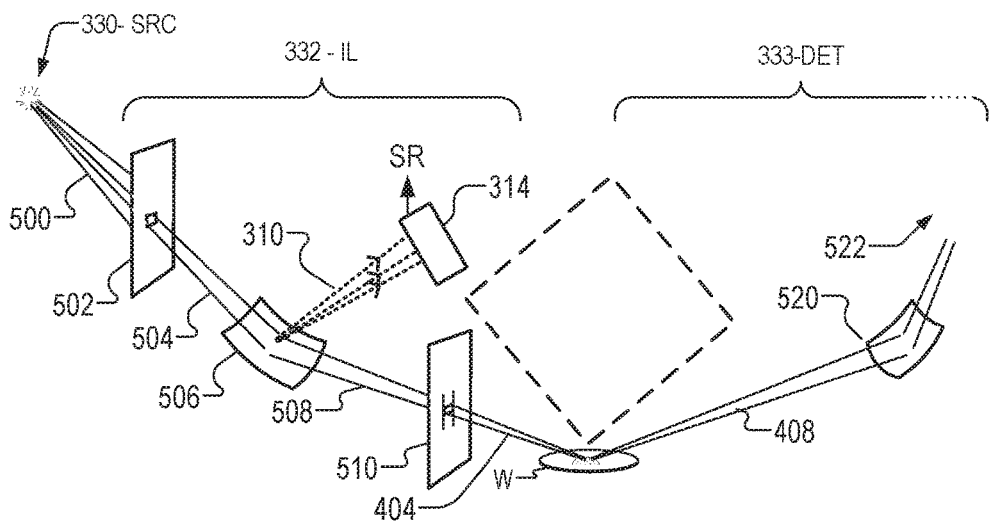
FIG. 5 illustrates schematically the components of an illumination system in the EUV metrology apparatus of FIG. 3.
Figure 10:
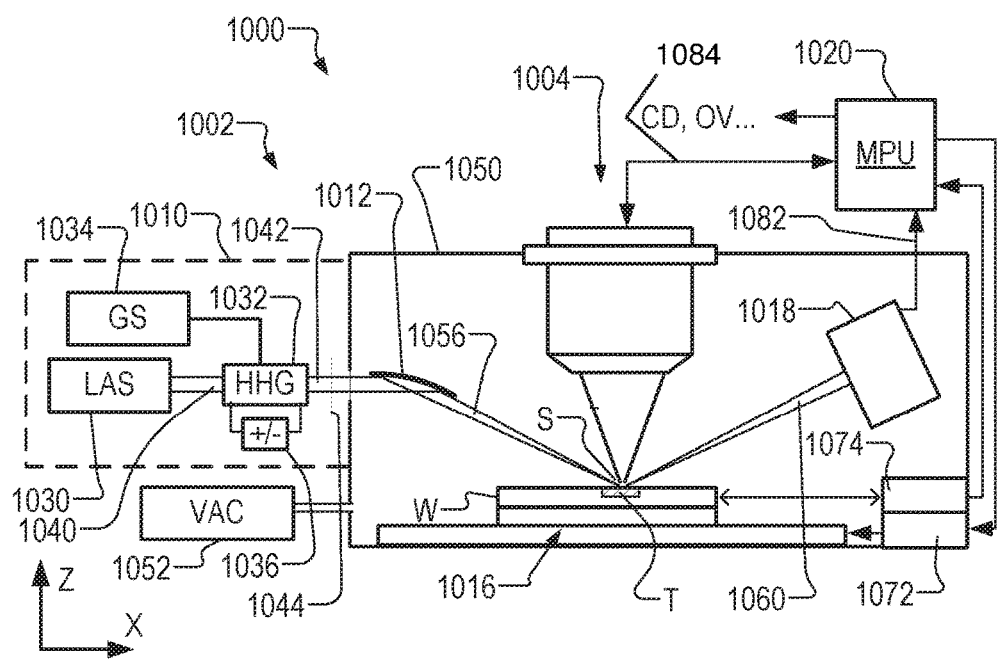
FIG. 10 illustrates a hybrid metrology apparatus including a scatterometer of the type shown in FIG. 9.

FIG. 5 illustrates one possible arrangement of the illumination system 332 in the EUV metrology apparatus of FIG. 3. A radiation source such as a plasma is represented at 330. For EUV lithography several types of sources have been tested and built experimentally or commercially. Any of these can be applied in the present apparatus, according to the range of wavelengths desired. Plasma sources include tin (Sn) but also Xe or Ar or Kr or Ne or N, or any combination of them. Laser driven light sources and harmonic generator sources can be applied. Plasma sources are not the only types of sources that can be applied. Synchrotron sources may yield more useful power levels, and be more controllable in wavelength and power, but these are not yet commercially available in a compact form. In some embodiments of the present disclosure, a higher harmonic generation (HHG) type of source may be used, or an inverse Compton scattering (ICS) source. An HHG source is illustrated in FIG. 10, described below.

A beam 500 of EUV radiation having desired spectral characteristics is emitted in a range of directions. At the exit of the source 330 (the entrance to the illumination system 332), a first aperture 502 is provided to serve as an entrance pupil for the illumination system. An incoming beam 504 with well-defined divergence impinges on a focusing optical element or system. This focusing system is implemented in the present illustration by a 2-dimensionally curved mirror 506, for example an ellipsoidal mirror. Mirror 506 produces a convergent beam 508, which is focused to form the spot at the target location on substrate W. Optionally, a second aperture 510 is provided to restrict the diameter of beam 404 at the target. In particular, aperture 510 may be made adjustable in height and/or width so that different shapes of beam B' can be generated according to different desires/sizes, and different incidence angles α.

Reflected beam 408 enters detection system 333 (not shown in this view), carrying information about the structure of the target. Optionally, a second focusing mirror 520 is provided to reduce divergence of the beam, as it enters detection system 333.

As seen in FIGS. 2 and 3, a reference spectrum 320 is formed and detected by reference spectrum detector 314. In the example illumination system illustrated in FIG. 5, the grating 318 for generating reference spectrum 320 is integrated in the curved mirror 506. In alternative embodiments, the reference spectrum grating could be provided as a separate element in series with the mirror 506. Further, in order to focus radiation from beam 504 into beam 508, the single two-dimensionally curved mirror 506 could be replaced by a series of two or more one-dimensionally curved (cylindrical) mirrors. The grating, wherever it is provided, may be of the "flat field" type, so that a well-resolved spectrum is formed across a linear or planar pixel array in detector 314. Similarly, where a two-dimensionally curved focusing mirror 520 is provided at a detection side, one or more dimensionally curved mirrors may be provided. The curved mirror can be integrated with the grating 312 which forms the spectrum 310 of the radiation reflected by the target. Note that it may not be necessary to focus the beam 408 in two dimensions in order to obtain a desired spectral resolution.

Also shown in FIG. 5 is the outline of a second metrology apparatus labelled 522. This illustrates where the illustrated layout allows space for a second illumination system and second detection system to work on the same target structure within the hybrid metrology apparatus 240.

In the pending European patent application 15160786 experimental results and simulations are presented to illustrate choices of wavelengths and choices of incidence angles that can be used in such an apparatus. Particularly in the wavelength range 15-40 nm and above 40 nm it is seen that the reflectance of several of the materials of interest remains substantial even up to angles of 10, 20 and 30 degrees. Referring again to FIGS. 4 and 5, this range of incidence angles allows an optical design to be implemented which achieves the desired small radiation spot, even at grazing incidence using available EUV optical technology.

Compared with X-rays of higher energy (shorter k), grazing incidence can be achieved at higher angles α in the EUV wavelengths 1-100 nm. The phenomenon of "total internal reflection" is familiar in optics at visible wavelengths, where a material such as glass has a refractive index greater than 1. At EUV wavelengths, materials generally have a refractive index less than 1, and the phenomenon of "total external reflection" results. The angle up to which significant reflection can obtained may be referred to as the critical angle. An advantage of the relatively shallow penetration depth at EUV wavelengths is that measurements can be obtained which represent the surface structure of the substrate, without significant interference of buried features which are commonly present in semi-conductor products. As explained further below, this shallow penetration depth can be exploited in one method of operation of a hybrid metrology system of FIG. 1.

The pending application also illustrates that penetration depth of EUV radiation varies with angle of incidence. For a given structure, a higher penetration depth can be achieved in the direction normal to the substrate, by elevating the angle α of incidence to a higher value. The range of incidence angles available to exploit this effect without losing reflectivity is higher in the EUV range, particularly in the range 15-100 nm, than it is for example in X-ray measurement techniques.

The pending application further explains by simulation and/or experiment how spectroscopic reflectometry in the EUV wavelength range can yield information on the form of a grating structure (periodic structure) formed on a silicon substrate. The calculations made confirm that good measurement information as to the presence and structure of a grating target should be obtainable by EUV spectroscopic reflectometry. Further calculations indicate that the detected spectra can reveal information about other parameters too, such as information about the side wall angle of the grating.

The calculations indicate that the strength of the signal carrying measurement information is greater as the angle of incidence α increases from 2° to 12°. Accordingly, depending on the material and structure to be measured, angles α of incidence of 5° or greater may be selected, for example angles in the range of 10 to 40 degrees. The optimum selection of angle will depend on the availability of spectral components in the source radiation, and on the reflectivity versus angle of incidence of different materials. That is to say, the angle of incidence should be selected as a compromise between the strength of the signals, and the strength of reflection by the particular materials of a target. Similarly, the strength of the signal (sidewall angle information) varies across the wavelength range. The incidence angle(s) and wavelength range(s) at which measurements will be performed can be selected to define an optimum metrology parameter set for a particular type of target and a particular property of interest. This metrology parameter set can be referred to as a metrology "recipe".

As is known, EUV optical apparatus cannot work in normal atmospheric environments. The pending application illustrates schematically the housing of different parts of an EUV metrology apparatus. This has features to facilitate management of vacuum and low pressure atmospheres within the apparatus, particularly in a high-volume manufacturing environment. In the event that the entire apparatus would be housed in a vacuum environment, the cost and time delay required to re-establish the vacuum environment after loading and unloading a wafer or bath of wafers would seriously degrade throughput. At the same time, it may be desirable to have as much as possible of the beam paths in a high vacuum environment. Different parts of the EUV optical system are contained in different chambers. Suitable walls may define these chambers, while windows permit EUV radiation to pass between the chambers. In the examples described in the pending patent application, a first chamber contains the radiation source and illumination system. A first atmospheric condition, for example high vacuum, is maintained in the first chamber. In a second chamber the substrate with a target structure is supported on a substrate support, where second atmospheric condition is maintained surrounding the target. The second atmospheric condition may be, for example, a low pressure gaseous atmosphere, for example using Hydrogen, Argon. In this way, when substrates are exchanged through some form of air lock mechanism, the required atmospheric condition can be established and re-established relatively quickly, and without undue cost. While transmission losses in the second atmospheric condition may be greater than in high vacuum, for the limited distance of travel and the operational productivity, these losses can be tolerated. Components of a detection system such as grating 312 and detector 313 are located in a third chamber, which is maintained at a third atmospheric condition. The third atmospheric condition may be for example a high vacuum.

Figure 6:
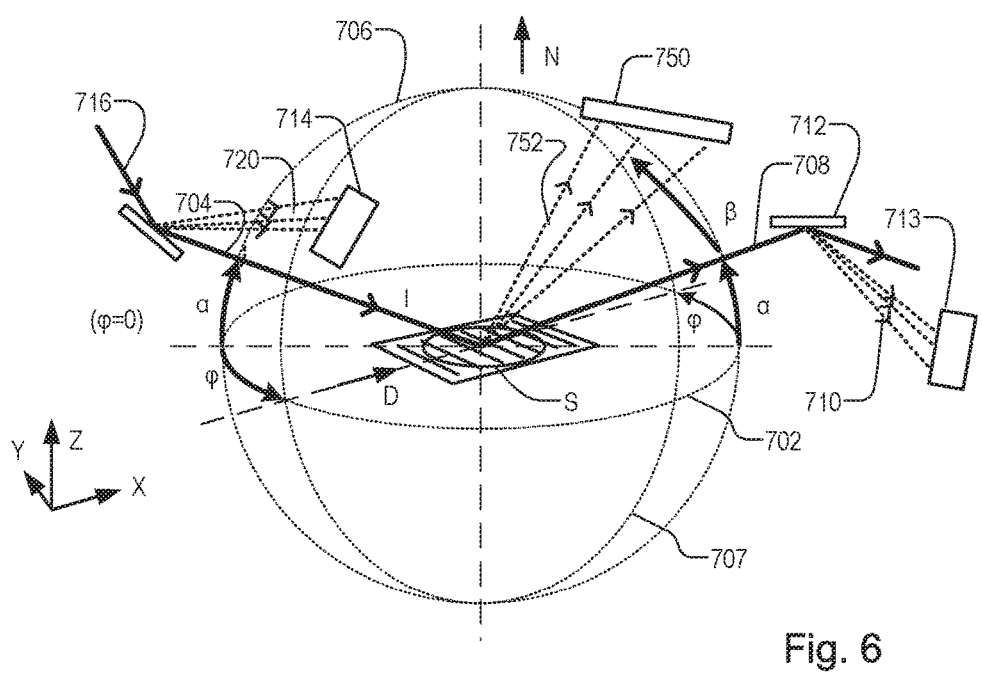
FIG. 6 illustrates the geometry of incident and reflected rays in relation to a grating target in a metrology method according to a another metrology apparatus usable in a hybrid metrology apparatus according to the present invention.
Figure 7:
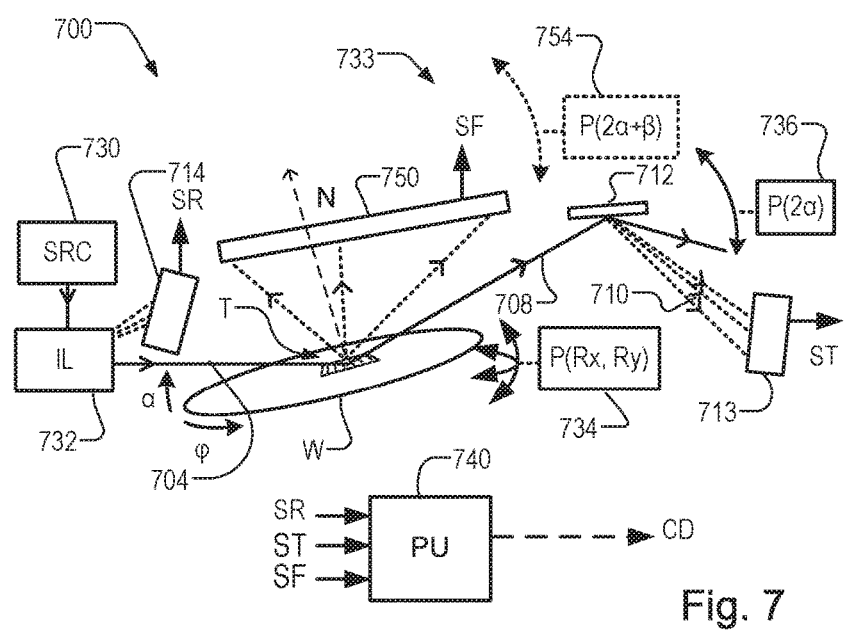
FIG. 7 illustrates schematically the components of a metrology apparatus, performing the method of FIG. 6.

FIG. 6 illustrates a further modified example of an EUV metrology method and FIG. 7 illustrates a corresponding metrology apparatus. This method and apparatus combine certain modifications described in more detail in the pending application mentioned above. Components labeled '7xx' in these examples should be considered to be the same as those labeled '3xx' in the methods and apparatuses of FIGS. 2 to 5. Thus the modified EUV metrology apparatus includes, for example, an illumination system 730, illumination system 732 and detection system 733.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. Detection system 733 again comprises a diffraction grating 712 to split the reflected rays 708 into a spectrum 710 of different wavelengths. The reflection spectrum 710 is captured by detector 713 and signals ST are provided to processor 740. Compared with the apparatus of FIG. 2, however, positioning system 734 is operable so that the angle of incidence of incident ray 704 can be varied not only in a grazing incidence angle $\alpha$, but also in an azimuthal angle, here labeled $\varphi$.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. However, a non-zero azimuthal angle of incidence $\varphi$ is allowed. The azimuthal angle $\varphi$ is de-fined relative to the direction of periodicity D of the grating target T. (In the case of a two-dimensionally periodic target, D may be either of the principal directions of periodicity.) That is to say, when the direction of incidence is projected onto the plane of the substrate, the azimuth-al angle $\varphi$ between the incident ray and the direction of periodicity D is non-zero, and may be very substantial. That is to say, the direction of irradiation lies outside a plane defined by the direction of periodicity D and the direction N normal to the substrate. Rather, the incident ray travels in a plane oblique to the direction of periodicity D. The oblique plane is represented by a circle 707 that is orthogonal to the plane of the substrate but oblique to the direction of periodicity and the X-Z plane. It will be understood that, while the choice of labels of planes and axes is arbitrary, the grazing incidence angle and azimuthal angle are defined with reference to physical properties of the periodic structure of the target.

As explained in the pending application, the diffraction efficiency of different diffraction orders can be increased substantially when non-zero azimuthal angles are used. This in turn has an impact on the spectrum of the reflected (zero order) ray 708.

In implementing the apparatus 700, different arrangements of positioning system can be used to achieve the non-zero azimuthal angle. Reference 734 indicates a positioning subsystem with actuators for rotation about the X and Y axes of the substrate. For a desired combination of grazing incidence angle $\alpha$ and azimuthal angle $\varphi$, appropriate command values Rx and Ry are calculated to cause tilting of the substrate in two dimensions to achieve the desired angles. In another implementation, actuators may be provided for rotation and tilting, directly driving the angles $\alpha$ and $\varphi$. As will be appreciated from FIG. 7, rotation Rz corresponds directly to a desired azimuthal angle $\varphi$, and command values in this case can be generated more directly from the desired measurement angles.

In other areas of metrology, the type of mounting required to vary both the grazing incidence (polar) angle and the azimuthal angle is known as a "conical mount", and that term can be adopted in this EUV reflectometry apparatus also. In general, the skilled reader will appreciate that any form of command and any form of actuating mechanism can be used to implement this example, provided it is suitable to achieve a known non-zero azimuthal angle of incidence. It will also be understood that the relative orientation of the direction of incidence and the target is what matters (and of course the correct X-Y positioning of the target relative to the radiation spot S).

In addition, in this modified method and apparatus 700, a third detector 750 is provided to receive another spectrum 752. Spectrum 752 comprises radiation diffracted at first order by the periodic structure of the target T. The angle $\beta$ at which the first order diffracted radiation is directed depends on the pitch of the target grating as well as the wavelength of the diffracted radiation. In the case of spectroscopic EUV reflectometry, where the incident radiation comprises a range of wavelengths, then radiation diffracted by the target spreads into a spectrum at a range of angles (3, as shown. This first order spectrum, like the reflection spectrum 710, contains information about the target structure. Signals SF which are captured by detector 750 are supplied to processor 740 for use (together with signals SR and ST), in calculating an improved measurement of a property of interest of the target.

Capturing first order diffraction spectra may have particular benefit in resolving properties of the target which are associated with asymmetry. Such a property is overlay.

While the range of angles $\beta$ is shown as quite a narrow range in FIG. 16, for convenience, it will be understood that quite a wide range of angles, including "backwards" diffraction, may be encountered. This is particularly the case because (i) the range of wavelengths of interest may span more than one octave (for example the ranges 10 to 40 nm or even 5 to 50 nm are mentioned in the examples above) and (ii) the pitch of the finest target gratings (which may be product features) will be similar in magnitude to the wavelength of the radiation, in a number of potential applications. FIG. 7 illustrates this range of angles. Referring to angle $\beta'$, defined relative to the normal direction N, a range of angles from $-90°$ to $+20°$ may be expected to arise, for example.

In order to accommodate wide variations in the diffraction angle $\beta$ (or $\beta'$), a further actuator 754 may be provided to move the detector 750 to an appropriate position, as the grazing incidence angle $\alpha$ varies by actuator 734 and as the first order diffraction angle $\beta$ varies with grating pitch and wavelength. Alternatively or in addition, detector 750 may be made large in ex-tent, and/or placed close to the substrate in the vicinity of the target. This is shown schematically in FIG. 7. Collimating optics may optionally be provided to reduce the spread of angles, if desired, so that they can be captured on a conveniently sized and conveniently placed detector 750. In the hybrid metrology system 240 disclosed herein, the detector 750 and any second or further metrology apparatus should be designed so as not to clash with each other.

Second Metrology Apparatus Examples

Figure 8:
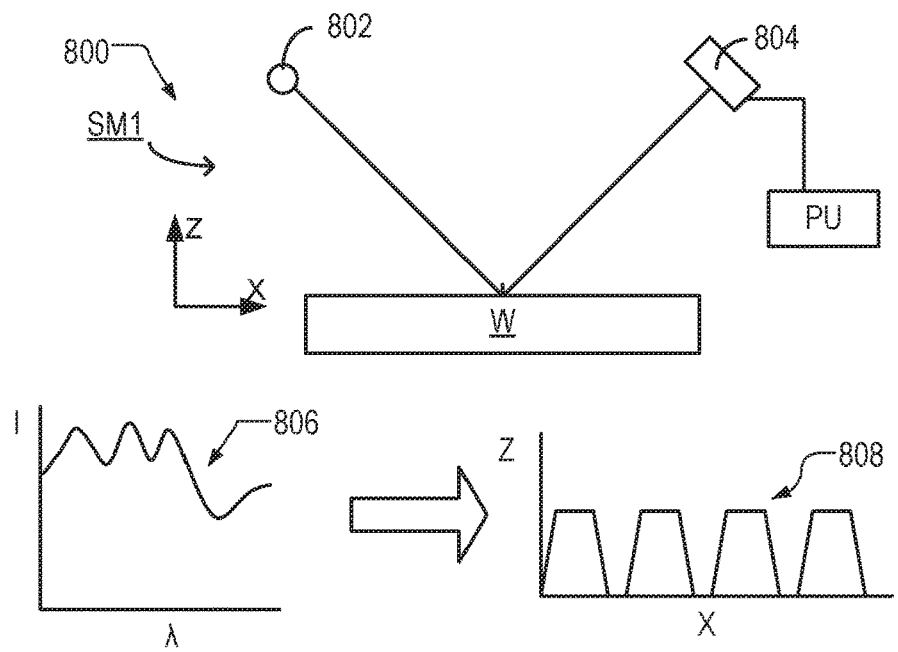
FIG. 8 depicts a spectroscopic scatterometer that may be used in metrology methods according to embodiments of the invention.

FIG. 8 depicts a known spectroscopic scatterometer 800 which may be used as one of the metrology apparatuses in a hybrid metrology system 240 of the type described above. It comprises a broadband (white light) radiation projector 802 which projects radiation onto a substrate W. The reflected radiation is passed to a spectrometer 804, which measures a spectrum 806 (intensity as a function of wavelength) of the specular reflected radiation. From this data, the structure or profile 8 giving rise to the detected spectrum may be reconstructed by calculation within processing unit PU. Processing unit PU may be part of the metrology processing unit 246, or it may be in a processor local to apparatus 800. Such a scatterometer may be configured as a normal-incidence scatterometer or an oblique-incidence scatterometer.

Figure 9:
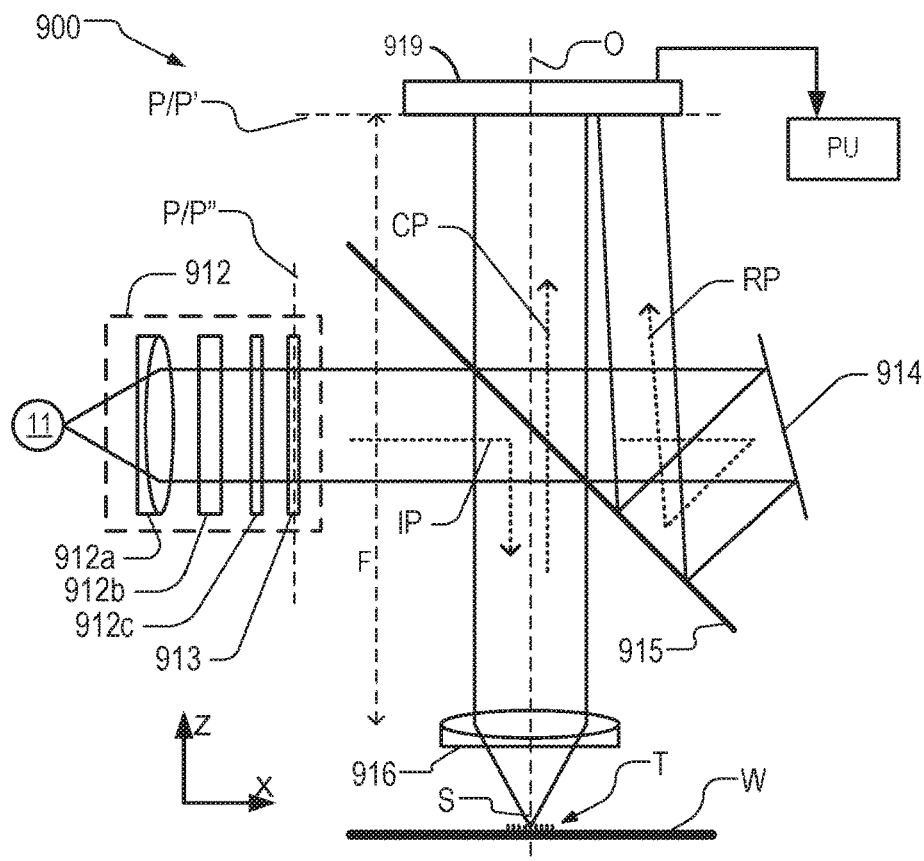
FIG. 9 depicts a second type of scatterometer that may be used in metrology methods according to embodiments of the invention.

FIG. 9 shows the basic elements of a known angle-resolved scatterometer 900 that may be used as one of the metrology apparatuses in a hybrid metrology system 240 of the type described above. In this type of metrology apparatus, radiation emitted by a radiation source 11 is conditioned by an illumination system 912. For example, illumination system 912 may include a collimating using lens system 912a, a color filter 912b, a polarizer 912c and an aperture device 913. The conditioned radiation follows an illumination path IP, in which it is reflected by partially reflecting surface 915 and focused into a spot S on substrate W via a microscope objective lens 916. A metrology target T may be formed on substrate W. Lens 916, has a high numerical aperture (NA), preferably at least 0.9 and more preferably at least 0.95. Immersion fluid can be used to obtain with numerical apertures greater than 1, if desired.

In other examples of an angle-resolved scatterometer, reflective optics may be used, instead of the refractive optics illustrated. The example of FIG. 9 may operate using wavelengths in near-UV, visible and/or near infrared ranges, for example from 350 nm to 1000 nm. For shorter ultraviolet wavelengths, for example in the DUV or VUV range 100 nm to 300 nm, reflective optics become more practical and a controlled atmospheric environment becomes necessary too. The NA of such systems may be lower. On the other hand, the spacing of optical components in a reflective optical system may make it easier to integrate first and second metrology apparatuses into the hybrid metrology system 240.

As in the lithographic apparatus LA, one or more substrate tables may be provided to hold the substrate W during measurement operations. The substrate tables may be similar or identical in form to the substrate tables WTa, WTb of FIG. 1. (In an example where the inspection apparatus is integrated with the lithographic apparatus, they may even be the same substrate tables.) Coarse and fine positioners may be configured to accurately position the substrate in relation to a measurement optical system. Various sensors and actuators are provided for example to acquire the position of a target of interest, and to bring it into position under the objective lens 916. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system are being brought to different locations on the substrate, when in practice the optical system remains substantially stationary and only the substrate moves. Provided the relative position of the substrate and the optical system is correct, it does not matter in principle whether one or both of those is moving in the real world.

When the radiation beam is incident on the beam splitter part of it is transmitted through the beam splitter (partially reflecting surface 915) and follows a reference path RP towards a reference mirror 914.

Radiation reflected by the substrate, including radiation diffracted by any metrology target T, is collected by lens 916 and follows a collection path CP in which it passes through partially reflecting surface 915 into a detector 919. The detector may be located in the back-projected pupil plane P, which is at the focal length F of the lens 916. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target T can be measured. In the pupil plane or conjugate pupil plane, the radial position of radiation defines the angle of incidence/departure of the radiation in the plane of focused spot S, and the angular position around an optical axis O defines azimuth angle of the radiation. The detector 919 may be, for example, an array of CCD or CMOS sensors, and may use an integration time of, for example, 40 milliseconds per frame.

Radiation in reference path RP is projected onto a different part of the same detector 919 or alternatively on to a different detector (not shown). A reference beam is often used for example to measure the intensity of the incident radiation, to allow normalization of the intensity values measured in the scatter spectrum.

The various components of illumination system 912 can be adjustable to implement different metrology 'recipes' within the same apparatus. Color filter 912b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 912c may be rotatable or swappable so as to implement different polarization states in the radiation spot S. Aperture device 913 can be adjusted to implement different illumination profiles. Aperture device 913 is located in a plane P''' conjugate with pupil plane P of objective lens 916 and the plane of the detector 919. In this way, an illumination profile defined by the aperture device defines the angular distribution of light incident on substrate radiation passing through different locations on aperture device 913.

The detector 919 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic-polarized light and transverse electric-polarized light.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes. The techniques disclosed herein are not limited to inspection of grating structures, and any target structure, including a blank substrate or a substrate having only flat layers on it, is included within the term "target structure".

In addition to measurement of parameters by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 9 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the example of FIG. 9, where detector 919 may be an image sensor, such asymmetry in the diffraction orders appears directly as asymmetry in the pupil image recorded by detector 919. This asymmetry can be measured by digital image processing in unit PU, and calibrated against known values of overlay. In the hybrid metrology system, measurements of asymmetry can be improved using spectra from more than one metrology apparatuses 242, 244.

As is also known, an inspection apparatus implementing angle-resolved scatterometry can be provided with adaptations for performing so-called dark field imaging. These are not illustrated here, for conciseness. Examples of dark-field imaging applied to overlay measurements on small targets are known from patent publications mentioned in the introductions, and incorporated herein by reference. A dark-field imaging branch can be combined with optical systems for acquiring target positions prior to angle-resolved scatterometry, and for focusing the spot S during capture of spectra. Different modes of illumination are possible by using different apertures 913.

Hybrid Metrology System Example

FIG. 10 illustrates in schematic form hybrid metrology system 1000 as an example of the hybrid metrology system 240 of FIG. 1. The hybrid metrology system may be a stand-alone device or incorporated in either the lithographic apparatus LA, or the lithographic cell LC. The apparatus may of course be used in conjunction with other apparatuses such as SEM apparatus, as part of a larger metrology system.

Hybrid metrology system 1000 in this example includes a first metrology apparatus 1002 using EUV radiation in grazing incidence, which may be similar to the apparatuses 300 or 700 above. A second metrology apparatus 1004 is provided in the form of a scatterometer, which may be similar to the apparatus 900 of FIG. 9. First metrology apparatus 1002 comprises a first radiation source 1010, first illumination system 1012, substrate support 1016, first detection system 1018 and processor 1020. Source 1010 in this example comprises for example a generator of EUV or x-ray radiation based on high harmonic generation (HHG) techniques. Such sources are available for example from KMLabs, Boulder Colo., USA (http://www.kmlabs.com/). Main components of the radiation source are a pump laser 1030 and an HHG gas cell 1032. A gas supply 1034 supplies suitable gas to the gas cell, where it is optionally ionized by an electric source 1036. The pump laser may be for example a fiber-based laser with an optical amplifier, producing pulses of infrared radiation lasting less than 1 ns (1 nanosecond) per pulse, with a pulse repetition rate up to several megahertz, as required. The wavelength may be for example in the region of 1 µm (1 micron). The laser pulses are delivered as a first radiation beam 1040 to the HHG gas cell 1032, where a portion of the radiation is converted to higher frequencies the first radiation into a beam 1042 including coherent radiation of the desired EUV wavelength or wavelengths.

The radiation may contain multiple wavelengths. If the radiation is also monochromatic, then measurement calculations (reconstruction) may be simplified, but it is easier with HHG to produce radiation with several wavelengths. These are matters of design choice, and may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. One or more filtering devices 1044 may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the beam path may be contained within a vacuum environment, bearing in mind that EUV radiation is absorbed when traveling in air. The various components of radiation source 1010 and illumination optics 1012 can be adjustable to implement different metrology 'recipes' within the same apparatus. For example different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and so-called x-ray lasers. A source based on inverse Compton scattering could also be used. Depending on the materials of the structure under inspection, different wavelengths may offer a desired level of penetration into lower layers. For resolving the smallest device features and defects among the smallest device features, then a short wavelength is likely to be preferred. A wavelengths in the range 1-20 nm or 1-10 nm may be chosen, for example. Wavelengths shorter than 5 nm suffer from very low critical angle when reflecting off materials typically of interest in semiconductor manufacture. Therefore to choose a wavelength greater than 5 nm will provide stronger signals at higher angles of incidence. On the other hand, if the inspection task is for detecting the presence of a certain material, for example to detect contamination, then wavelengths up to 50 nm could be useful.

From the first radiation source 1010, the filtered beam 1042 enters an inspection chamber 1050 where the substrate W including a structure of interest is held for inspection by substrate support 1016. The structure of interest is labeled T. The atmosphere within inspection chamber 1050 is maintained near vacuum by vacuum pump 1052, so that EUV radiation can pass without undue attenuation through the atmosphere. The Illumination optics 1012 has the function of focusing the radiation into a focused beam 1056, and may comprise for example a two-dimensionally curved mirror, or a series of one-dimensionally curved mirrors, as described above. The focusing is performed to achieve a round or elliptical spot under 10 µm in diameter, when projected onto the structure of interest. Substrate support 1016 comprises for example an X-Y translation stage and a rotation stage, by which any part of the substrate W can be brought to the focal point of beam to in a desired orientation. Thus the radiation spot S is formed on the structure of interest.

Reflected radiation 1060 is captured by detector 1018 and a first spectrum is provided to processor 1020 for use in calculating a property of the target structure T. The first illumination system 1012 and first detection system 1018 thus form a first metrology apparatus. This first metrology apparatus may comprise an EUV spectroscopic reflectometer of the kind shown in FIGS. 2 to 7. Tilting of the substrate in one or more dimensions may also be provided.

A second metrology apparatus 1004 within the hybrid metrology system is indicated schematically at 1004. This apparatus includes a second radiation source (not shown separately), a second illumination system (not shown separately) and a separate detector (not shown separately). These components may for example be the same as the illumination system and detection system of a spectroscopic scatterometer of FIG. 8, an angle-resolved scatterometer of FIG. 9, a spectroscopic ellipsometer, and/or a spectroscopic Mueller ellipsometer. The optical design may be adapted to use reflective optics if required. The second metrology apparatus 1004 may alternatively or in addition include EUV metrology apparatus. For example, it may use EUV radiation to perform spectroscopic reflectometry in the same way as the example first metrology apparatus, but with different incidence angles closer to normal direction N.

To aid the alignment and focusing of the spot S with desired product structures, second metrology apparatus 1004 may also provide auxiliary optics using auxiliary radiation under control of metrology processor 1020. Metrology processor 1020 can also communicate with a position controller 1072 which operates the translation stage and rotation stages. Processor 1020 receives highly accurate feedback on the position and orientation of the substrate, via sensors. Sensors 1074 may include interferometers, for example, which can give accuracy in the region of picometers.

In the operation of the hybrid metrology system 1000, first spectrum data 1082 captured by first detection system 1018 is delivered to metrology processing unit 1020. Second spectrum data 1084 captured by second detection system within second metrology apparatus 1004 is delivered to metrology processing unit 1020 and used together with the first spectrum data to calculate one or more measurements of parameters of interest. As will be explained, the manner of combining the data can be different from that in known hybrid metrology systems. For example, based on spectrum data obtained from one of the metrology apparatuses, a metrology recipe of the other metrology apparatus may be adjusted, before a spectrum is captured by that other apparatus. Alternatively or in addition, spectrum data obtained from one of the metrology apparatuses may be used to characterize structures and/or materials of part of the complete target structure T, prior to calculating property of the structure using spectrum data obtained from the other metrology apparatus. All these operations may be automated by metrology processor 1020.

Figure 11A:
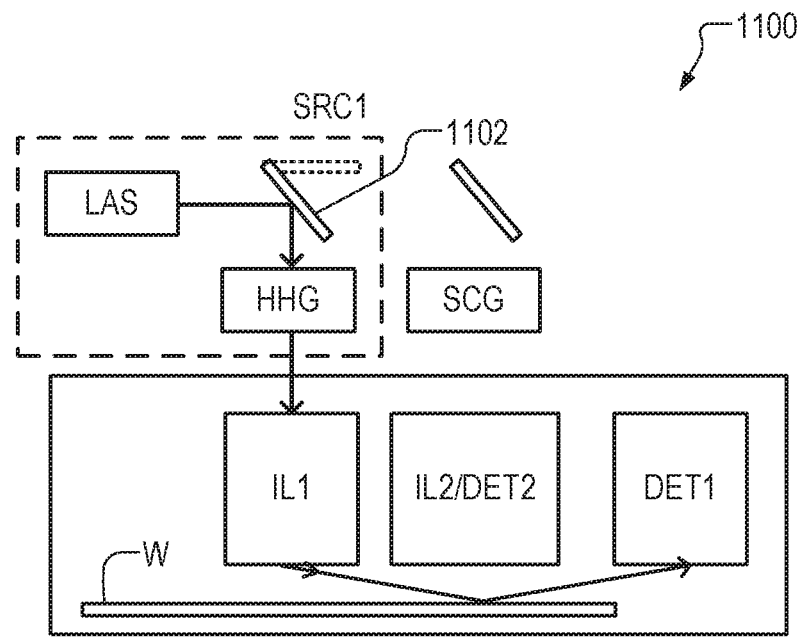
FIGS. 11A-11B shows a radiation source arrangement for a hybrid metrology apparatus, in which a pump laser is shared between EUV (FIG. 11A) and longer-wave radiation sources (FIG. 11B)

FIG. 11 illustrates an example of a hybrid metrology system 1100 in which part of a first radiation source is shared with a second radiation source. It will be appreciated that provision of multiple radiation sources within a single hybrid metrology system may be challenging in terms of cost and physical space. Particularly for those modern sources that provide high brightness and/or control of wavelengths, a pump laser is provided. The pump laser may be designed to generate pulses in the femtosecond time range. An example of a radiation source using a pump laser is the higher harmonic generation (HHG) source illustrated in FIG. 10. Another example is a supercontinuum source, used to provide broadband radiation in known scatterometers.

Figure 11B:
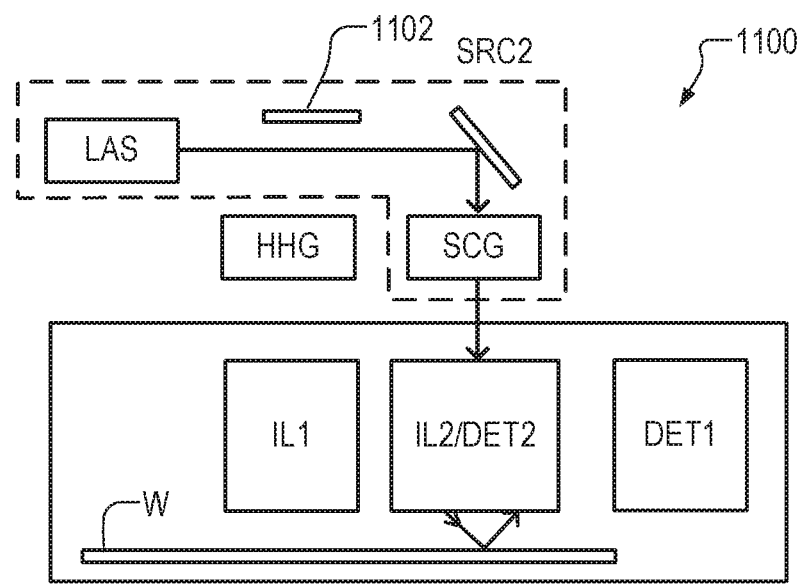

In FIG. 11 we see the hybrid metrology system modes of operation (a) and (b). Within a main body of the system, a first illumination system IL1 and a first detection system DET1 form a first metrology apparatus, which may be an EUV spectroscopic reflectometer. Between these components, a second illumination system IL2 and second detection system DET2 are provided to form a second metrology apparatus. In FIG. 11 (a), the first metrology apparatus is operating using an HHG source. A movable mirror 1102 is positioned to direct pump radiation from pump laser LAS into an HHG cell. First radiation is generated in the HHG cell so as described above, and then into the first illumination system ILL In FIG. 11(b), the second metrology apparatus is operating using for example a supercontinuum generator SCG. An element used for this purpose is, for example, a photonic crystal fiber. Movable mirror 1102 is moved to a second position so that radiation from pump laser LAS enters the super continuum generator. This generates second radiation to be supplied to the second illumination system IL2.

Application Examples

Figure 12:
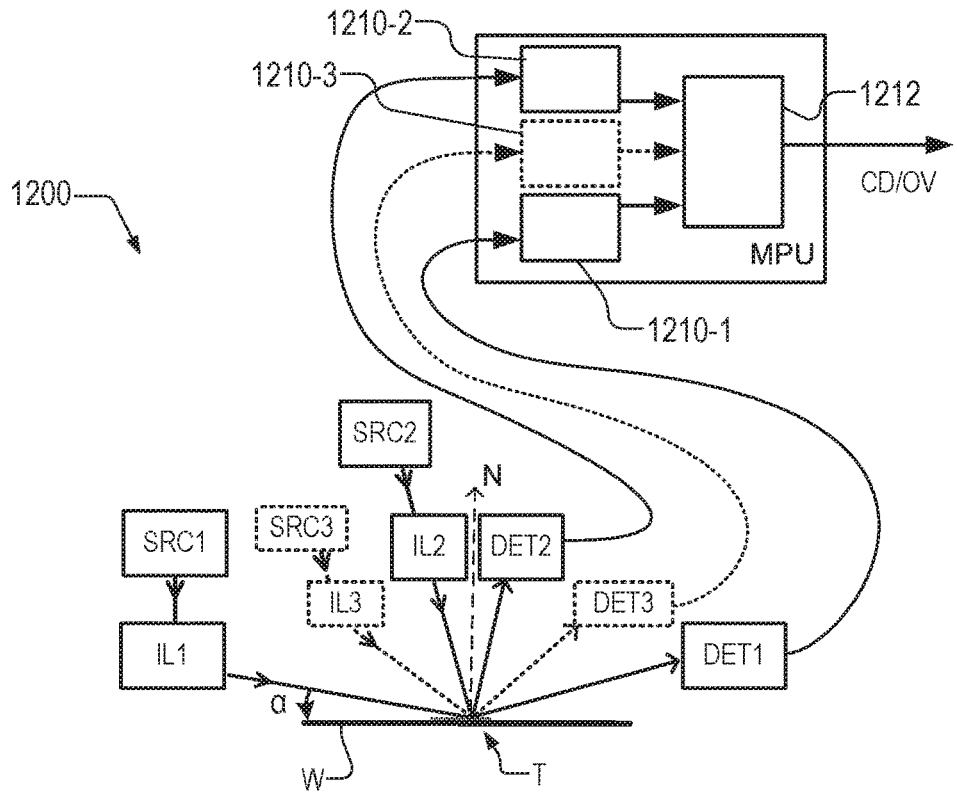
FIG. 12 shows a general arrangement of metrology apparatuses and data flow in a first example hybrid metrology apparatus in the production facility shown in FIG. 1.

FIG. 12 shows a generic example of a hybrid metrology system in which first, second and optionally third metrology apparatuses are provided. Each metrology apparatus comprises a source SRC1/2/3, an illumination system IL1/2/3 and a detection system DET1/2/3. A hybrid metrology apparatus can be produced which includes both EUV metrology apparatus 244 for performing and longer-wavelength optical metrology apparatus 240 for performing more conventional scatterometry measurements. Both apparatuses may work simultaneously on the same parts or different parts of a same substrate W. The two apparatuses may in practice operate at different times, while sharing common components such as substrate handling and positioning systems. The metrology apparatuses may be integrated with either the lithographic apparatus LA itself or within the lithographic cell LC. Within the metrology processing unit MPU, dedicated modules 1210-1/2/3 are provided to process to some extent spectrum data received from each of the detection systems DET1/2/3. Preprocessed results are delivered from these dedicated modules to a hybrid processing module 1212, which combines information from the individual spectra to obtain the measurement of the desired parameter of target structure T.

Figure 13:
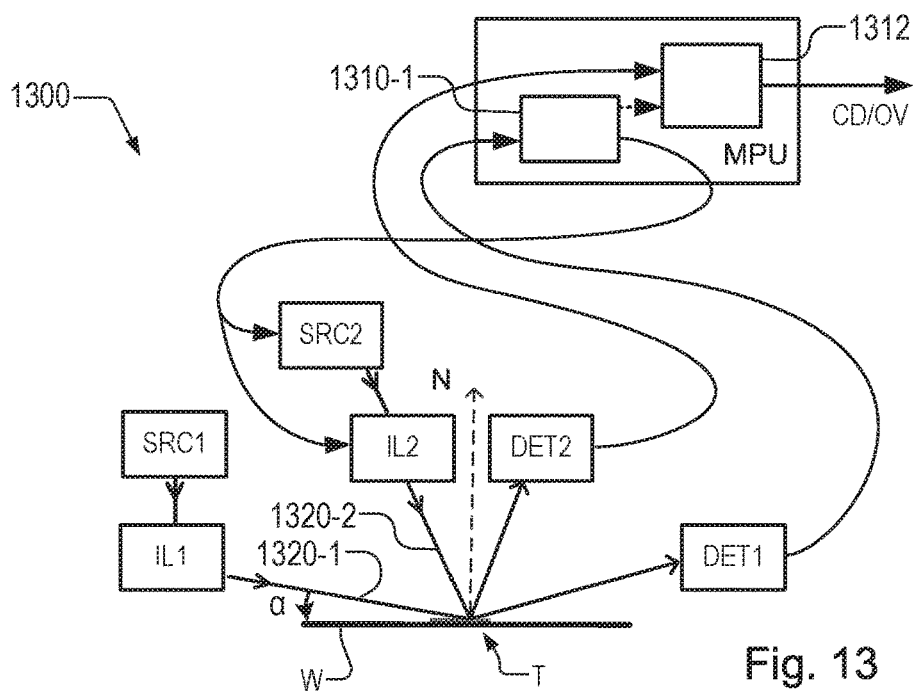
FIG. 13 shows a general arrangement of metrology apparatuses and data flow in a second example hybrid metrology apparatus in the production facility shown in FIG. 1.

FIG. 13 shows another example of a hybrid metrology system 1300. In this example, a dedicated processing module 1310-1 receives first spectrum data captured by first detection system DET1 using first radiation 1320-1. This first spectrum data may be, for example, spectroscopic reflectometer data from a grazing incidence EUV radiation beam. This first spectrum data may include zero order and/or higher-order spectra, using one of the apparatuses of FIGS. 2 to 7. The second metrology apparatus, is then operated using radiation 1320-2 and second spectrum data is captured by second detection system DET2. Before operating the second metrology apparatus, however, settings of the second radiation source SRC2 and/or second illumination system IL2 are sent in response to parameters calculated by processing module 1310-1.

After operating the second metrology apparatus, second spectrum data is processed by a hybrid processing module 1312 to obtain the measurement of the desired parameter of target structure T. In some embodiments, the first spectrum data may be directly or indirectly combined with the second spectrum data in hybrid processing module 1312. For example, the first spectrum data may be used to vary parameters of processing a second spectrum data. In other embodiments, it may be that the first spectrum data is obtained solely for controlling the recipe for obtaining the second spectrum data, and is not directly used in obtaining the final measurement.

Particularly with reference to the examples of FIGS. 12 to 15, the methods and apparatus described herein can be applied also to the measurement of asymmetry-related features, such as overlay. Overlay between layers in a semiconductor product may be difficult to measure using EUV spectroscopic reflectometry at some incidence angles and/or wavelengths, because of the shallow penetration depth of radiation. Nevertheless, by providing the illustrated apparatus with a broad range of wavelengths (for example 1-100 nm) and with the possibility to use elevated incidence angles in a second metrology apparatus, practical measurements of overlay may be expected.

Figure 14A:
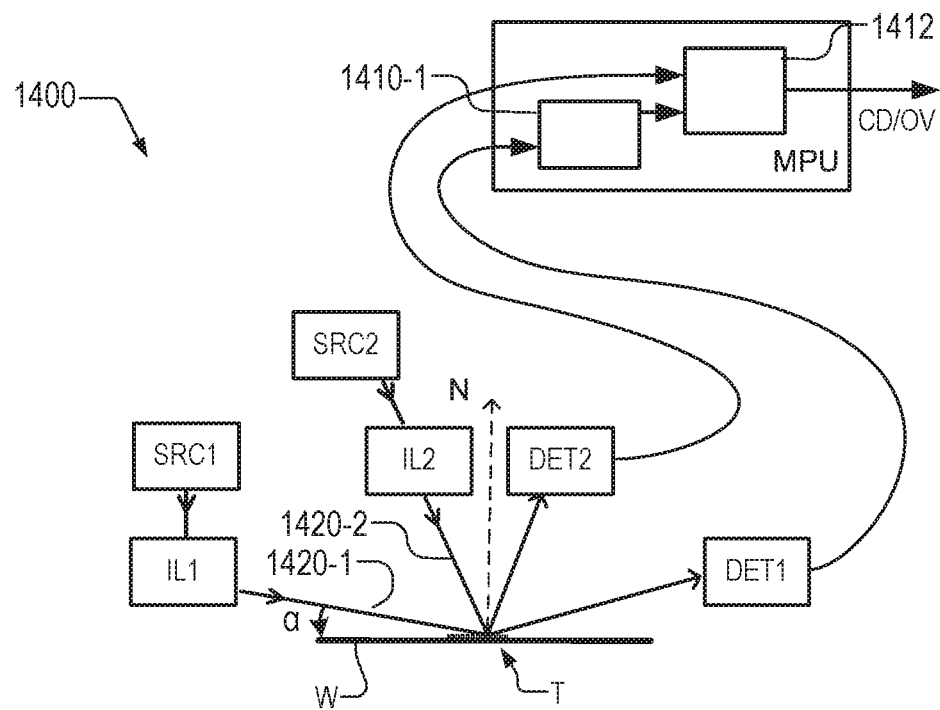
FIG. 14A shows a general arrangement of metrology apparatuses and data flow in a third example hybrid metrology apparatus in the production facility shown in FIG. 1.
Figure 14B:
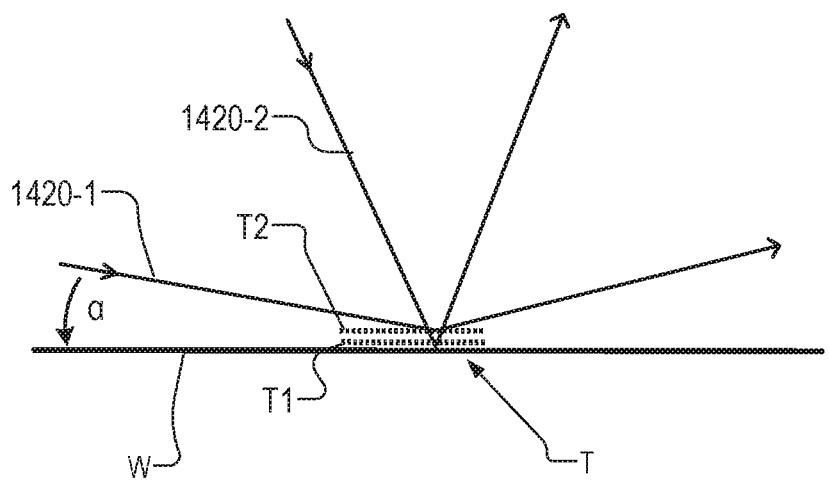
FIG. 14B shows interaction of grazing incidence radiation and normal incidence radiation with an overlay target structure in the example of FIG. 14 (*a*)

FIG. 14 shows another example of a hybrid metrology system 1400. In one embodiment of this example, the parameter of interest is related to asymmetry of the target structure, for example to obtain a measure of overlay. As shown at FIG. 14(*b*), target structure T may comprise grating features T1 and a lower layer, and T2 in an upper layer. Either or both of these structures may be buried beneath further layers, not shown. When measuring overlay, the reported measurement known methods can be very sensitive to asymmetry not caused by overlay as such. Application of hybrid metrology techniques using the system of FIG. 14 can help to isolate those effects which are truly due to the parameter of interest from those having other causes.

One way in which accuracy of an overlay measurement can be improved can be seen in the enlarged schematic detail of FIG. 14 (*b*). First radiation 1420-1 used in a first metrology apparatus has grazing incidence and penetrates very little into a stack of layers formed on substrate W. First spectrum data is captured by first detection system DET1 with little influence from the lower layers Properties of the upper layer containing grating features T2 can then be measured and reported by dedicated module 1410-1. Second radiation 1420-2 having a higher angle of incidence, and possibly having different wavelength characteristics and other properties, penetrates more fully into the stack. Consequently, second spectrum data contains asymmetry information related to the parameter of interest, specifically overlay. Combining the processing of these spectra in the hybrid processing module 1412, the overlay measurement that is carried in the second spectrum can be adjusted to remove the influence of the lower layers, using the knowledge gained from the first spectrum.

Overlay between layers is just one example of an asymmetry-related parameter of a target structure. In a multiple-patterning process, structures are formed in one layer of the product not in one patterning operation but in two or more patterning steps. Thus, for example, a first population of structures may be interleaved with a second population of structures, and the populations are formed in different steps, so as to achieve a higher resolution than one step alone can produce. While the placement of the populations should be identical and perfect in relation to other features on the substrate, of course every real pattern exhibits a certain positional offset. Any unintentional positional offset between the populations can be regarded as a form of overlay, and can be measured by asymmetry of the target grating or product features formed by multiple patterning processes. Other types of asymmetry, for example sidewall asymmetry and trench bottom asymmetry can also be measured, for a simple grating structure. Furthermore, using the hybrid metrology system is described herein, crosstalk between these different asymmetry-related parameters of can be reduced, to isolate measurements of a parameter of interest.

While asymmetry can be measured from (zero order) reflection spectra 310, 710 (in the examples of FIGS. 3 and 7), asymmetry information will be stronger in the first order diffracted spectra 752 detected in the example of FIG. 7. Accordingly, a method of EUV metrology may include using signals SF representing first order diffraction spectra from a periodic structure to measure asymmetry in the structure. The structure may be measured in one orientation only, or it may be measured in orientations rotated (Rz) by 180°. As is known from diffraction based overlay at visible wavelengths, the asymmetry can be calculated by comparing the intensity of +1 and −1 order diffracted radiation. By rotating the target through 180°, signals SF(+1) and SF(−1) can be obtained and compared. Asymmetry can be calculated like any other property of the target, by a reconstruction method. Alternatively, simpler calculations, combined with prior calibration, can be based more directly on comparing the +1 and −1 order spectra. However, using full reconstruction, in combination with the spectroscopic approach, the information available may assist a more accurate measurement than simply comparing +1 and −1 order intensities at a single wavelength. In EUV reflectometry, it is an advantage that the target can be made of product features or product-like features, which is not possible with current optical techniques using longer wavelengths. Sensitivity to overlay is expected to be greater than current tools. By combining different types of measurement in the hybrid metrology system of FIG. 14, further improvements in accuracy can be obtained.

Using modern laser-pumped sources such as the HHG and ICS types mentioned above, high power can be provided in one or more desired wavelengths, compared with conventional sources. Adequate penetration into the stack can thus be obtained, even with a single wavelength in the EUV patent. Of course, the second radiation may be longer in wavelengths than EUV radiation. Penetration and contrast may be increased by moving to longer wavelengths, while spatial resolution may be lost as a compromise. Using the principles disclosed herein and the sources and optical systems described, the skilled person has a full range of options to choose from in designing an effective hybrid metrology system.

Any of the apparatuses 300, 700 can be used as (EUV) first metrology apparatus 244 in a lithographic production facility system such as is illustrated schematically in FIG. 1

Figure 15:
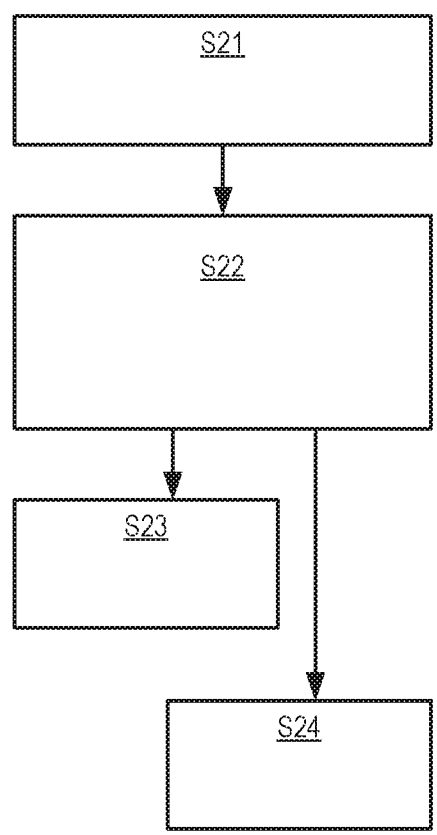
FIG. 15 is a flow chart illustrating a method of controlling performance of a metrology method and/or of a lithographic manufacturing process using measurements made by the hybrid metrology system of FIG. 1.

FIG. 15 illustrates the application of a hybrid measurement method (for example any of the methods of FIGS. 10 to 14) in the management of a lithographic manufacturing system. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the EUV metrology apparatus 244 and the other metrology apparatus 240 and information sources are used to measure a property of the structures across the substrate. At step S23, optionally, metrology recipes and calibrations of the EUV metrology apparatus 244 and/or other metrology apparatus 240 are updated in light of the measurement results obtained. For example, where the EUV metrology apparatus 244 has a lower throughput than the optical metrology apparatus 240, a few accurate measurements using EUV radiation can be used to improve the calculation of measurements made using the optical metrology apparatus, for a specific substrate design and process.

At step S24, measurements of CD or other parameters are compared with desired values, and used to update settings of the lithographic apparatus and/or other apparatus within the lithographic manufacturing system. By providing an EUV metrology apparatus as part of a hybrid metrology system, throughput and/or accuracy can be improved and the performance of the whole lithographic production facility can be improved. Product features and/or product-like features can be measured directly, even at the smallest technology nodes, and in-die targets can be provided and measured without losing too much area.

In the above steps, it is assumed that sufficient targets are measured across a substrate and across multiple substrates, that statistically reliable models of the process are derivable. The profile of CD and other parameters does not need to be expressed entirely as a variation across the substrate. It can be expressed for example as an intra-field profile that is common to all fields (each instance of patterning using the patterning device M at a different location on the substrate W) and a lower order, inter-field, variation onto which the intra-field variation is repeatedly superimposed. The settings of the lithographic process adjusted in step S24 can include intra-field settings as well as inter-field settings. They may be applicable to all operations of the apparatus, or specific to a particular product layer.

CONCLUSION

While specific embodiments of the invention have been described above, it will be appreciated that the invention may be practiced otherwise than as described. In association with the novel targets as realized on substrates and patterning devices, an embodiment may include a computer program containing one or more sequences of machine-readable instructions describing a methods of, measuring targets on a substrate and/or processing measurements to obtain information about a lithographic process. This computer program may be executed for example within unit MPU 246 in the production facility of FIG. 1. There may also be provided a data storage medium (e.g., semiconductor memory, magnetic or optical disk) having such a computer program stored therein.

Although patterning devices in the form of a physical reticle have been described, the term "patterning device" in this application also includes a data product conveying a pattern in digital form, for example to be used in conjunction with a programmable patterning device.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the current invention are presented in below numbered clauses:

1. A hybrid metrology apparatus for measuring a property of a structure manufactured by a lithographic process, the hybrid metrology apparatus comprising:
   (a) a first illumination system for irradiating the structure with first radiation, the first radiation comprising one or more wavelengths in the range 1 nm to 100 nm;
   (b) a first detection system for detecting a first spectrum comprising at least part of the first radiation reflected by the periodic structure;
   (c) a second illumination system for irradiating the structure with second radiation, the second radiation comprising one or more wavelengths in the range 1 nm to 100 nm or in the range 100 nm to 1000 nm;
   (d) a second detection system for detecting a second spectrum comprising at least part of the second radiation reflected by the periodic structure;
   (e) a processing system for using the detected first spectrum and the detected second spectrum to determine a property of the structure.

2. A system according to clause 1 wherein the processing system is arranged to use the detected first spectrum to control one or more parameters of the second illumination system and/or the second detection system for the capture of the second spectrum.

3. A system according to clause 1 wherein the processing system is arranged to use the detected second spectrum to control one or more parameters of the first illumination system and/or the first detection system for the capture of the first spectrum.

4. A system according to any preceding clause wherein for the first radiation a grazing angle of incidence α relative to a direction parallel to the substrate is less than 45 degrees, while for the second radiation polar angle of incidence θ relative to a direction normal to the substrate is less than 45 degrees.

5. A system according to clause 4 wherein the grazing angle of incidence is greater than 2 degrees.

6. A system according to clause 4 wherein the grazing angle of incidence for the first radiation is between 5° and 45°, optionally between 10° and 30°.

7. A system according to clause 4, 5 or 6 wherein the grazing angle of incidence for the first radiation is adjustable as a parameter of a metrology recipe.

8. A system according to any preceding clause wherein the first radiation when projected onto the structure has an extent less than 10 optionally less than 5 μm.

9. A system according to any preceding clause wherein an azimuthal angle of incidence of the first radiation is adjustable as a parameter of a metrology recipe.

10. A system according to any preceding clause wherein the first radiation sequentially or concurrent comprises a range of wavelengths, and wherein the first detection system is a spectroscopic detection system, the first spectrum representing a distribution of wavelengths in said reflected first radiation.

11. A system according to clause 10 wherein the first detection system is further arranged to capture a higher order spectrum representing a distribution of wavelengths in one or more higher diffraction orders diffracted by a the structure.

12. A system according to any preceding clause wherein the second detection system is a spectroscopic detection system, the second spectrum representing a distribution of wavelengths in the reflected first radiation.

13. A system according to any preceding clause wherein the second detection system is an angle-resolved detection system, the first spectrum representing a distribution of diffracted radiation in the reflected first radiation.

14. A system according to any preceding clause wherein the second radiation comprises one or more wavelengths in the range 100 nm to 1000 nm.

15. A system according to clause 14 wherein the second radiation comprises one or more wavelengths in the range 350 nm to 900 nm.

16. A system according to any of clauses 1 to 13 wherein the second radiation comprises one or more wavelengths in the range 1 to 100 nm.

17. A system according to any preceding clause wherein said processor is arranged to use the first spectrum and second spectrum to determine a property of a structure having one or more upper layers and one or more lower layers, and wherein said processor is arranged to use said first spectrum to distinguish properties of the upper layer from properties of the structure as a whole.

18. A system according to any preceding clause wherein said property of the structure is related to asymmetry.

19. A system according to clause 18 wherein said property of the structure is overlay between sub-structures in the upper and lower layers.

20. A system according to any preceding clause further comprising a first radiation source for generating said first radiation and a second radiation source for generating said first radiation.

21. A system according to clause 20 wherein said first radiation source and said second radiation source share a pump laser.

22. A system according to clause 20 or 21 wherein said first radiation source is a higher harmonic generator source.

23. A system according to clause 20, 21 or 22 wherein said second radiation source is a higher harmonic generator source.

24. A system according to any of clauses 20 to 23 wherein said second radiation source is a supercontinuum source.

25. A system according to any of clauses 20 to 23 wherein said first radiation source and/or said second radiation source is an inverse Compton scattering source.

26. A method of measuring a property of a structure manufactured by a lithographic process, the method comprising:
(a) irradiating the structure with first radiation, the first radiation comprising one or more wavelengths in the range 1 nm to 100 nm;
(b) detecting a first spectrum comprising at least part of the first radiation reflected by the periodic structure;
(c) irradiating the structure with second radiation, the second radiation comprising one or more wavelengths in the range 1 nm to 100 nm or in the range 100 nm to 1000 nm;
(d) detecting a second spectrum comprising at least part of the second radiation reflected by the periodic structure;
(e) using the detected first spectrum and the detected second spectrum to determine a property of the structure.

27. A method according to clause 26 wherein step (e) is performed so as to use the detected first spectrum to control one or more parameters of the second irradiating step (c) and/or the second detecting step (d) for the capture of the second spectrum.

28. A method according to clause 26 wherein step (e) is performed so as to use the detected second spectrum to control one or more parameters of the first irradiating step (a) and/or the first detecting step (b) for the capture of the first spectrum.

29. A method according to any of clauses 26 to 28 wherein for the first radiation a grazing angle of incidence α relative to a direction parallel to the substrate is less than 45 degrees, while for the second radiation polar angle of incidence θ relative to a direction normal to the substrate is less than 45 degrees.

30. A method according to clause 29 wherein the grazing angle of incidence is greater than 2 degrees.

31. A method according to clause 29 wherein the grazing angle of incidence for the first radiation is between 5° and 45°, optionally between 10° and 30°.

32. A method according to clause 29, 30 or 31 wherein the grazing angle of incidence for the first radiation is adjusted as a parameter of a metrology recipe.

33. A method according to any of clauses 26 to 32 wherein the first radiation when projected onto the structure has an extent less than 10 μm, optionally less than 5 μm.

34. A method according to any of clauses 26 to 33 wherein an azimuthal angle of incidence of the first radiation is adjusted as a parameter of a metrology recipe.

35. A method according to any of clauses 26 to 34 wherein the first radiation sequentially or concurrent comprises a range of wavelengths, and wherein the first detecting step (b) uses a spectroscopic detection system, the first spectrum representing a distribution of wavelengths in said reflected first radiation.

36. A method according to clause 10 wherein the first detecting step (b) further comprises capturing a higher order spectrum representing a distribution of wavelengths in one or more higher diffraction orders diffracted by a the structure.

37. A method according to any of clauses 26 to 36 wherein the second detecting step (d) uses a spectroscopic detection system, the second spectrum representing a distribution of wavelengths in the reflected first radiation.

38. A method according to any of clauses 26 to 37 wherein the second detecting step (d) uses an angle-resolved detection system, the first spectrum representing a distribution of diffracted radiation in the reflected first radiation.

39. A method according to any of clauses 26 to 38 wherein the second radiation comprises one or more wavelengths in the range 100 nm to 1000 nm.

40. A method according to clause 39 wherein the second radiation comprises one or more wavelengths in the range 350 nm to 900 nm.

41. A method according to any of clauses 26 to 38 wherein the second radiation comprises one or more wavelengths in the range 1 to 100 nm.

42. A method according to any of clauses 26 to 41 wherein the first spectrum and second spectrum are used to determine a property of a structure having one or more upper layers and one or more lower layers, and wherein step (e) includes using said first spectrum to distinguish properties of the upper layer from properties of the structure as a whole.

43. A method according to any of clauses 26 to 42 wherein said property of the structure is related to asymmetry.

44. A method according to clause 43 wherein said property of the structure is overlay between sub-structures in the upper and lower layers.

45. A device manufacturing method comprising:
transferring a pattern from a patterning device onto a substrate using a lithographic process, the pattern defining at least one periodic structure;
measuring one or more properties of the periodic structure to determine a value for one or more parameters of the lithographic process; and
applying a correction in subsequent operations of the lithographic process in accordance with the measured property, wherein the step of measuring the properties of the periodic structure includes measuring a property using the hybrid metrology apparatus according to any of clauses 1 to 25.

46. A device manufacturing method according to clause 45 wherein said functional device pattern defines product features having a critical dimension less than 50 nm, optionally less than 20 nm.

47. A device manufacturing method comprising:
transferring a pattern from a patterning device onto a substrate using a lithographic process, the pattern defining at least one periodic structure;
measuring one or more properties of the periodic structure to determine a value for one or more parameters of the lithographic process; and
applying a correction in subsequent operations of the lithographic process in accordance with the measured property,
wherein the step of measuring the properties of the periodic structure includes measuring a property using the method according to any of clauses 26 to 44.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 1-100 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A hybrid metrology apparatus for measuring a property of a structure manufactured by a lithographic process, the hybrid metrology apparatus comprising:
a first illumination system configured to irradiate the structure with first radiation, the first radiation comprising one or more wavelengths in the range 1 nm to 100 nm;
a first detection system configured to detect a first spectrum comprising at least part of the first radiation reflected by the structure;
a second illumination system configured to irradiate the structure with second radiation, the second radiation comprising one or more wavelengths in the range 1 nm to 100 nm or in the range 100 nm to 1000 nm;
a second detection system configured to detect a second spectrum comprising at least part of the second radiation reflected by the structure; and
a processing system configured to use the detected first spectrum and the detected second spectrum to determine a property of the structure.

2. The system of claim 1, wherein the processing system is arranged to use the detected first spectrum to control one or more parameters of at least one of the second illumination system and the second detection system for the capture of the second spectrum.

3. The system of claim 1, wherein the processing system is arranged to use the detected second spectrum to control one or more parameters of at least one of the first illumination system and the first detection system for the capture of the first spectrum.

4. The system of claim 1, wherein:
the first illumination system is further configured to cause the first radiation to be incident to the substrate with a grazing angle of incidence $\alpha$ relative to a direction parallel to the substrate that is less than 45 degrees; and
the second illumination system is further configured to cause the second radiation to be incident to the substrate with a polar angle of incidence $\theta$ relative to the direction normal to the substrate that is less than 45 degrees.

5. The system of claim 1, wherein:
the first radiation sequentially or concurrent comprises a range of wavelengths, and
the first detection system is a spectroscopic detection system, the first spectrum representing a distribution of wavelengths in the reflected first radiation.

6. The system of claim 1, wherein the second detection system is a spectroscopic detection system, the second spectrum representing a distribution of wavelengths in the reflected first radiation.

7. The system of claim 1, wherein the second detection system is an angle-resolved detection system, the first spectrum representing a distribution of diffracted radiation in the reflected first radiation.

8. The system of claim 1, wherein:
the processor is arranged to use the first spectrum and second spectrum to determine a property of a structure having one or more upper layers and one or more lower layers, and
the processor is arranged to use the first spectrum to distinguish properties of the upper layer from properties of the structure as a whole.

9. The system of claim 1, further comprising a first radiation source configured to generate the first radiation and a second radiation source for generating the second radiation.

10. The system of claim 9, wherein the first radiation source and the second radiation source share a pump laser.

11. A method of measuring a property of a structure manufactured by a lithographic process, the method comprising:
irradiating the structure with first radiation, the first radiation comprising one or more wavelengths in the range 1 nm to 100 nm;
detecting a first spectrum comprising at least part of the first radiation reflected by the structure;
irradiating the structure with second radiation, the second radiation comprising one or more wavelengths in the range 1 nm to 100 nm or in the range 100 nm to 1000 nm;

detecting a second spectrum comprising at least part of the second radiation reflected by the structure; and determining a property of the structure based on the detected first spectrum and the detected second spectrum.

12. The method of claim 11, wherein the determining is performed so as to use the detected first spectrum to control one or more parameters of the second irradiating or the second detecting for the capture of the second spectrum.

13. The method of claim 11, wherein the determining is performed so as to use the detected second spectrum to control one or more parameters of the first irradiating or the first detecting for the capture of the first spectrum.

14. The method of claim 11, wherein for the first radiation a grazing angle of incidence α relative to a direction parallel to the substrate is less than 45 degrees, while for the second radiation polar angle of incidence θ relative to a direction normal to the substrate is less than 45 degrees.

15. The method of claim 11, wherein:
the first radiation sequentially or concurrent comprises a range of wavelengths, and
the first detecting uses a spectroscopic detection system, the first spectrum representing a distribution of wavelengths in the reflected first radiation.

16. The method of claim 11, wherein:
the first spectrum and second spectrum are used to determine a property of a structure having one or more upper layers and one or more lower layers, and
the determining includes using the first spectrum to distinguish properties of the upper layer from properties of the structure as a whole.

17. The method of claim 11, wherein the property of the structure is related to asymmetry.

18. The method of claim 17, wherein the property of the structure is overlay between sub-structures in an upper layer and sub-structures in a lower layer.

19. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the measuring the properties of the structure includes measuring a property using the hybrid metrology apparatus comprising:
a first illumination system configured to irradiate the structure with first radiation, the first radiation comprising one or more wavelengths in the range 1 nm to 100 nm;
a first detection system configured to detect a first spectrum comprising at least part of the first radiation reflected by the structure;
a second illumination system configured to irradiate the structure with second radiation, the second radiation comprising one or more wavelengths in the range 1 nm to 100 nm or in the range 100 nm to 1000 nm;
a second detection system configured to detect a second spectrum comprising at least part of the second radiation reflected by the structure; and
a processing system configured to use the detected first spectrum and the detected second spectrum to determine a property of the structure.

20. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the measuring the properties of the structure includes measuring a property using a method comprising:
irradiating the structure with first radiation, the first radiation comprising one or more wavelengths in the range 1 nm to 100 nm;
detecting a first spectrum comprising at least part of the first radiation reflected by the structure;
irradiating the structure with second radiation, the second radiation comprising one or more wavelengths in the range 1 nm to 100 nm or in the range 100 nm to 1000 nm;
detecting a second spectrum comprising at least part of the second radiation reflected by the structure; and
determining a property of the structure based on the detected first spectrum and the detected second spectrum.

* * * * *